United States Patent
Hanuš et al.

(10) Patent No.: US 6,552,192 B1
(45) Date of Patent: Apr. 22, 2003

(54) SUBSTITUTED NITROGEN HETEROCYCLIC DERIVATIVES AND PHARMACEUTICAL USE THEREOF

(75) Inventors: Jan Hanuš, Praha (CZ); Vladimír Kryštof, Ostrava (CZ); Marián Hajdúch, Olomouc (CZ); Jaroslav Veselý, Bohunovice (CZ); Miroslav Strnad, Olomouc (CZ)

(73) Assignee: Ustau Experimentalni Botaniky AV-CR, Praha (CZ)

( * ) Notice: Subject to any disclaimer, the term of this patent is extended or adjusted under 35 U.S.C. 154(b) by 0 days.

(21) Appl. No.: 09/889,176

(22) PCT Filed: Jan. 25, 2000

(86) PCT No.: PCT/CZ00/00002
§ 371 (c)(1),
(2), (4) Date: Jul. 12, 2001

(87) PCT Pub. No.: WO00/43394
PCT Pub. Date: Jul. 27, 2000

(30) Foreign Application Priority Data

Jan. 26, 1999 (CZ) .......................................... PV-273-99

(51) Int. Cl.⁷ .................... C07D 487/04; C07D 473/16; A61K 31/52; A61P 35/00; A61P 37/06
(52) U.S. Cl. ...................... 544/280; 544/244; 544/276; 544/277; 546/118
(58) Field of Search ................................ 544/280, 244; 514/258, 81, 765.1

(56) References Cited

U.S. PATENT DOCUMENTS

| | | | | |
|---|---|---|---|---|
| 4,923,872 A | * | 5/1990 | Kostlan et al. ............. | 544/280 |
| 5,236,926 A | * | 8/1993 | Josyula et al. ............. | 544/280 |
| 5,514,688 A | * | 5/1996 | Borcherding et al. ........ | 514/300 |
| 5,650,511 A | * | 7/1997 | Elliott et al. ............. | 544/280 |
| 6,281,220 B1 | * | 8/2001 | Yuan et al. ............... | 514/265.1 |
| 2002/0022632 A1 | * | 2/2002 | Bakthavatchalam ......... | 514/258 |

FOREIGN PATENT DOCUMENTS

EP 374096 * 12/1989

OTHER PUBLICATIONS

Girson, J. CHem. Soc. Perkins I, 3025 (1998).*
Bisagni, J. Org. Chem 47, 1500 (1982).*
Montagnier, Chem Abs 82: 118797m (1974).*
Bennett, Jr, J. Pharmacology and Experimental Therapeutics 266, 707–714 (1993).*

* cited by examiner

*Primary Examiner*—Mark L. Berch
(74) *Attorney, Agent, or Firm*—Notaro & Michalos P.C.

(57) ABSTRACT

Various substituted nitrogen heterocyclic derivatives and their pharmaceutically acceptable salt derivatives are provided for use as medicaments, and particularly, as antimitotic, anti-viral, anti-cancer, anti-degenerative, immunosuppressive, and anti-microbial drugs or vaccines. These heterocyclic derivatives can be used as an active agent in a pharmaceutical, as well as a diagnostic utility. To this end, several families of heterocyclic derivatives are provided including pyrrolopyrimidines, pyrazolopyrimidines, purines, and imidazopyridines. In particular, certain tri-substituted and tetra-substituted purines and pyrazolopyrimidines and their deaza analogues are provided for inhibiting cyclin-dependent kinase ("cdk") proteins, viruses, and immunostimulation.

30 Claims, No Drawings

SUBSTITUTED NITROGEN HETEROCYCLIC DERIVATIVES AND PHARMACEUTICAL USE THEREOF

FIELD OF THE INVENTION

This invention relates to new purine and pyrazolopyrimidine derivatives and their deaza analogues and to their use in suitable utilities, especially diagnostic and therapeutic methods.

It relates, in particular, to purine derivatives and their inhibitory effect with respect to cyclin-dependent kinase proteins, abbreviated cdks and also with an inhibitory effect with respect to viruses and immunostimulation. Purine analogues as cdk inhibitors are disclosed for example in WO 97/16452, WO 98/05335 and WO/9720842. The teaching of these patents includes 2,6,9-trisubstituted and less substituted purine derivatives only.

DESCRIPTION OF RELATED ART

Tetrasubstituted purines are disclosed in WO 98/01448 in which substituents are short hydrocarbonyl chains, usually represented by hydrogen. Substituents at C6 represents hydrogen or amine optionally substituted by one or two hydrocarbon groups; substituents at C8 are hydroxy, mercapto, acyloxy or oxycarbonyl substituted by aliphatic alkyl only. Nucleotide analogues containing phosphonate groups are diclosed for example in U.S. Pat. Nos. 4,659,825; 4,724,233; 5,124,051; 5,302,585; 5,208,221; 5,352,786; 5,356,886;.5,142,051; in EP publication numbers 269,947; 481,214; 630,381; 369,409; 454,427; 618,214; 398,231; 454,427; 468,119; 481,119; 481,214; 434,450 and in WO 95/07920; WWO 094/03467, WO96/33200 and WO94/03467. Typical purine base is adenine, 2,6-diaminopurine and guanine. The purine bases may include the deaza analogues thereof 6,9-Substituted and 2,6,9-trisubstituted purines and related analogues are disclosed in WO 96/33200. 2,8,9-, 6,8,9-Trisubstituted and 2,6,8,9-tetrasubstituted purines and tri- and tetrasubstituted pyrazolopyrimidines and their deaza analogues have not yet been described.

SUMMARY OF THE INVENTION

It is an object of this invention to provide anticancer, antiviral, neurodepresssive and immunosuppressive compounds having improved selectivity and efficiency index, i.e. that are less toxic yet more efficacious than analogues known heretofore.

The invention concerns substituted nitrogen heterocyclic derivatives of the formula I

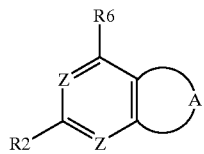

(I)

wherein,

A is a divalent group selected from the ensemble consisting of

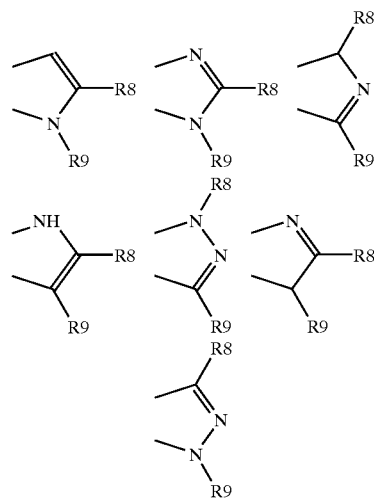

Z is N or CH, provided that at least one Z being N;

R2 and R6 are independent of one another, represent H, halogen, alkyl, substituted alkyl, cycloalkyl, substituted cycloalkyl, cycloalkyl alkyl, arylalkyl, heteroalkyl, heteroarylalkyl, cycloheteroalkyl alkyl or R6'—X wherein X is an —NH—, —N($C_1$–$C_6$-alkyl)-, —O— or —S— moiety;

R6' is H, alkyl, substituted alkyl, acyl, amido, sulfo, cycloalkyl, substituted cycloalkyl, aryl, substituted aryl, heterocycle, heteroaryl, substituted heteroaryl, arylalkyl, cycloheteroalkyl, substituted cycloheteroalkyl, heteroarylalkyl, heteroalkyl, cycloalkyl alkyl and cycloheteroalkyl alkyl;

R8 is halogen, hydroxyl, amino, carboxyl, cyano, nitro, amido, sulfo, sulfamido, carbamino, alkyl, substituted alkyl, cycloalkyl, substituted cycloalkyl, arylalkyl, heteroalkyl, heteroarylalkyl, cycloalkyl alkyl, cycloheteroalkyl alkyl or R8'—X wherein X is —NH—, —N(alkyl)-, —O— or —S— moiety and R8' is according to any one of the substituents defined above for R2' or R6'.

R9 is alkyl, substituted alkyl, acyl, carboxyl, amido, sulfamino, cycloalkyl, substituted cycloalkyl, cycloalkyl alkyl, heteroalkylcycloalkyl alkyl, heterocycloalkyl, substituted heterocycloalkyl, aryl, substituted aryl, heterocycle, heteroaryl, substituted heteroaryl, arylalkyl, heteroarylalkyl, heteroalkyl or —B—R9'— wherein B is —$CH_2$—, —$(CH_2)_2$—, —$CH(CH_3)CH_2$—, —$CH(CH_2F)CH_2$—, —$CH(CH_2OH)CH_2$—, or the groups of the following structure,

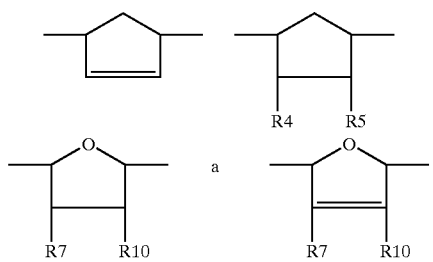

wherein the left hand bond is linked to nitrogen of 5-membered ring of compounds of the formula I;

R4 and R5, that are independent of one another, represent hydrogen, hydroxyl, halogen, amino, acyloxy substituent having 1–5 carbon atoms, alkoxy substituent having 1–5 carbon atoms, alkylmercapto substituent having 1–5 carbon atoms, alkylamino substituent having 1–5 carbon atoms and dialkylamino in which each alkyl substituent has 1–5 carbon atoms;

R7 and R10, that are independent of one another, represent H or alkyl substituent having 1–10 carbon atoms;

R9 is —$(CH_2)_n$—R9', wherein n=1–2 and the

R9' is —$X(CH_2)_m Y$ wherein

X is —O—, —S—, —NH— or —N (alkyl)- substituent having 1–6 carbon atoms;

m=1–2;

Y is carboxyl, amido, sulfo, sulfamino, hydroxyl, carboxyl, mercapto, carbylmercapto, amino, alkylamino, carbamino—$PO(OH)_2$, —$PO(O$—$C_1$–$C_6$-alkyl$)_2$, —$PO(NH$—$C1$–$C6$-alkyl$)_2$, $PO(O$—$C_1$–$C_6$-alkyl$)(NH$—$C1$–$C6$-alkyl$)$, —$PO(OH)(O$—$C_1$–$C_6$-alkyl$)$; —$PO(OH)(NH$—$C_1$–$C_6$-alkyl$)$ or —$(CH_2CHD)$—R9', wherein R9', X, m and Y are as defined above and D is alkyl, substituted alkyl, —$PO(OH)_2$, —$PO(OH)(O$—$C_1$–$C_6$-alkyl$)$, —$PO(OH)(NH$—$C_1$–$C_6$-alkyl$)$.

The above not yet defined generic group having meanings as introduced in the following legend:

"halogen" refers to fluorine, bromine, chlorine, and iodine atoms;

"alkyl" refers to
a branched or unbranched alkyl group having 1–6 carbon atoms,
a branched or unbranched alkenyl group having 1–6 carbon atoms,
a branched or unbranched alkinyl group having 1–6 carbon atoms;

"substituted alkyl" refers to a branched or unbranched alkyl, alkenyl or alkinyl group having 1–6 carbon atoms and having substituted by one or more substituents selected from the group consisting of hydroxyl, mercapto, carbylmercapto, halogen, carbyloxy, amino, amido, carboxyl, cycloalkyl, sulfo or acyl. These substituent generic groups having the meanings being identical with the definitions of the corresponding groups as defined in this legend;

"carbyloxy" denotes the group —$OR_a$, where $R_a$ is alkyl, substituted alkyl, aryl, substituted aryl, arylalkyl, substituted arylalkyl, cycloalkyl, substituted cycloalkyl, heterocycloalkyl or substituted heterocycloalkyl whereas these generic groups have meanings which are identical with definitions of the corresponding groups as defined in this, legend;

"carbylmercapto" denotes the group —$SR_b$, where $R_b$ is alkyl, substituted alkyl, aryl, substituted aryl, arylalkyl, substituted arylalkyl, cycloalkyl, substituted cycloalkyl, heterocycloalkyl or substituted heterocycloalkyl whereas these generic groups have meanings which are identical with definitions of the corresponding groups as defined in this legend;

"sulfo" denotes the group —$SO_3R_c$, where $R_c$ is
hydrogen,
a branched or unbranched alkyl group having 1–6 carbon atoms,
a branched or unbranched alkenyl group having 1–6 carbon atoms,
a branched or unbranched alkinyl group having 1–6 carbon atoms, a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulfo or acyl, whereas these generic groups have meanings which are identical with the definitions of the corresponding groups as defined in this legend;

"sulfamino" denotes the group —$NHSO_3R_d$, wherein $R_d$ is
hydrogen,
a branched or unbranched alkyl group having 1–6 carbon atoms
a branched or unbranched alkenyl group having 1–6 carbon atoms,
a branched or unbranched alkinyl group having 1–6 carbon atoms, a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulfo or acyl, whereas these generic substituents have meanings which are identical with definitions of the corresponding groups as defined in this legend;

"acyl" denotes the group —$C(O)R_e$, where $R_e$ is hydrogen, alkyl, substituted alkyl, aryl, substituted aryl, arylalkyl, substituted arylalkyl, cycloalkyl, substituted cycloalkyl whereas these generic groups have meanings which are identical with definitions of the corresponding groups as defined in this legend;

"aryloxy" denotes the group —OAr, where Ar is an aryl, substituted aryl, heteroaryl or substituted heteroaryl whereas these generic groups have meanings which are identical with definitions of the corresponding groups as defined in this legend;

"alkylamino" denotes the group —$NR_fR_g$, where $R_f$ and $R_g$, that are independent of one another, represent hydrogen, alkyl, substituted alkyl, aryl, substituted aryl, heteroaryl or substituted heteroaryl, whereas these generic substituents have meanings which are identical with definitions of the corresponding groups defined herein;

"amido" denotes the group —$C(O)NR_hR_i'$, where $R_h$ and $R_i'$ may independently be hydrogen, alkyl, substituted alkyl, aryl, substituted aryl, heteroaryl, substituted heteroaryl whereas these generic groups have meanings which are identical with definitions of the corresponding groups as defined in this legend;

"carboxyl" denotes the group —$C(O)OR_j$, where R is hydrogen, alkyl, substituted alkyl, aryl, substituted aryl, heteroaryl or substituted heteroaryl , whereas these generic substituents have meanings which are identical with definitions of the corresponding groups defined herein;

"carbamino" denotes the group —$NHCOR_k$, where $R_k$ may be hydrogen, alkyl, substituted alkyl, heterocycle, aryl, substituted aryl, heteroaryl and substituted heteroaryl whereas these generic groups have meanings which are identical with definitions of the corresponding groups as defined in this legend;

"aryl" refers to an aromatic carbocyclic group having from 1 to 18 carbon atoms and being composed of at least one aromatic or multiple condensed rings in which at least one of which being aromatic;

"substituted aryl" refers to an aromatic carbocyclic group having from 1 to 18 carbon atoms and being composed of at least one aromatic ring or of multiple condensed rings at least one of which being aromatic. The ring(s) are optionally substituted with one or more substituents selected from the group consisting of halogen, alkyl, hydroxyl, carbylmercapto, alkylamino, carbyloxy, amino, amido, carboxyl, nitro, mercapto or sulfo, whereas these generic substituent group have meanings which are identical with definitions of the corresponding groups as defined in this legend;

"heterocycle" refers to a heterocyclic group having from 4 to 9 carbon atoms and at least one heteroatom selected from the group consisting of N, O or S;

"heteroaryl" refers to a heterocyclic group having from 4 to 9 carbon atoms and at least one heteroatom selected from the group consisting of N, O or S with at least one ring of this group being aromatic;

"substituted heteroaryl" refers to a heterocyclic group having from 4 to 9 carbon atoms and at least one heteroatom selected from the group consisting of N, O or S with at least one ring of this group being aromatic and this group being substituted with one or more substituents selected from the group consisting of halogen, alkyl, carbyloxy, carbylmercapto, alkylamino, amido, carboxyl, hydroxyl, nitro, mercapto or sulfo, whereas these generic substituent group have meanings which are identical with definitions of the corresponding groups as defined in this legend;

"arylalkyl" denotes the group —$R_l$—Ar where $R_l$ is
  a branched or unbranched alkyl group having 1–6 carbon atoms,
  a branched or unbranched alkenyl group having 1–6 carbon atoms,
  a branched or unbranched alkinyl group having 1–6 carbon atoms,
and Ar is
  an aromatic carbocyclic group having from 1 to 18 carbon atoms and being composed of at least one aromatic ring or of multiple condensed rings at least one of which being aromatic and the group being optionally substituted with one or more substituents selected from the group consisting of halogen, alkyl, hydroxyl, carbylmercapto, alkylamino, carbyloxy, amino, amido, carboxyl, nitro, mercapto or sulfo, whereas these generic substituent group have meanings which are identical with definitions of the corresponding groups as defined in this legend;

"heteroalkyl" denotes the group —$R_m$—L where L is
  a branched or unbranched alkyl group having 1–6 carbon atoms,
  a branched or unbranched alkenyl group having 1–6 carbon atoms,
  a branched or unbranched alkinyl group having 1–6 carbon atoms,
  a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulfo or acyl, whereas these generic substituent group have meanings which are identical with definitions of the corresponding groups as defined in this legend
and L is
  a heterocyclic group having from 4 to 9 carbon atoms, and at least one heteroatom selected from the group consisting of N, O or S and the group being unsubstituted or substituted with one or more substituents selected from the group consisting of halogen, alkyl, alkoxy, alkylmercapto, alkylamino, amido, carboxyl, hydroxy, nitro, mercapto or sulfo, whereas these generic substituents have meanings which are identical with definitions of the corresponding groups as defined in this legend;

"heteroarylalkyl" denotes the group —$R_n$—G— where $R_n$ is
  a branched or unbranched alkyl group having 1–6 carbon atoms,
  a branched or unbranched alkenyl group having 1–6 carbon atoms,
  a branched or unbranched alkinyl group having 1–6 carbon atoms,
  a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulfo or acyl, whereas these generic substituent group have meanings which are identical with definitions of the corresponding groups as defined in this legend
and G is
  a heterocyclic group having from 4 to 9 carbon atoms and at least one heteroatom selected from the group consisting of N, O or S with at least one ring of which being aromatic and the group being optionally substituted with one or more substituents selected from the group consisting of halogen, alkyl, carbyloxy, carbylmercapto, alkylamino, amido, carboxyl, hydroxyl, nitro, mercapto or sulfo, whereas these generic substituent group have meanings which are identical with definitions of the corresponding groups as defined in this legend;

"cycloalkyl" refers to a monocyclic or polycyclic alkyl group containing 3 to 15 carbon atoms;

"substituted cycloalkyl" refers to a monocyclic or polycyclic alkyl group containing 3 to 15 carbon atoms and being substituted by one or more substituents selected from the group consisting of halogen, alkyl, substituted alkyl, carbyloxy, carbylmercapto, aryl, nitro, mercapto or sulfo, whereas these generic substituent groups have meanings which are identical with definitions of the corresponding groups as defined in this legend;

"heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P;

"substituted heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend;

"cycloalkyl alkyl" denotes the group —$R_o$—J where $R_o$ is
  a branched or unbranched alkyl group having 1–6 carbon atoms, a branched or unbranched alkenyl group having 1–6 carbon atoms, a branched or unbranched alkinyl group having 1–6 carbon atoms, a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulfo or acyl, whereas these generic substituent group have meanings which are identical with definitions of the corresponding groups as defined in this legend and J is a monocyclic or polycyclic alkyl group containing 3 to 15 carbon atoms;

a monocyclic or polycyclic alkyl group containing 3 to 15 carbon atoms which contains one or more substituents selected from the group consisting of halogen, alkyl, substituted alkyl, carbyloxy, carbylmercapto, aryl, nitro, mercapto or sulfo, whereas these generic substituent groups have meanings which are identical with definitions of the corresponding groups as defined in this legend and "heterocycloalkylalkyl" denotes the group —$R_p$V where $R_p$ is a branched or unbranched alkyl group having 1–6 carbon atoms, a branched or unbranched alkenyl group having 1–6 carbon atoms, a branched or unbranched alkinyl group having 1–6 carbon atoms, a branched or unbranched alkyl, alkenyl or alkinyl group having 1–6 carbon atoms and being substituted by one or more substituents selected from the group consisting of hydroxyl, mercapto, carbylmercapto, halogen, carbyloxy. amino, amido, carboxyl, cycloalkyl, sulfo or acyl, whereas. these generic substituent groups have meanings which are identical with definitions of the corresponding groups as defined in this legend and V is a monocyclic or polycyclic alkyl group containing 3 to 15 carbon atoms with at least one being replaced with a heteroatom selected from the group consisting of N, O, S or P;

a monocyclic or polycyclic alkyl group containing 3 to 15 carbon atoms with at least one being replaced with a heteroatom selected from the group consisting of N, O, S or P and the group contains one or more substituents selected from the group consisting of halogen, alkyl, substituted alkyl, carbyloxy, carbylmercapto, aryl, nitro, mercapto or sulfo, whereas these generic substituent groups have meanings which are identical with definitions of the corresponding groups as defined in this legend and the pharmaceutically acceptable acid salts, racemates and optical isomers thereof.

The invention concerns further substituted nitrogen heterocyclic derivatives of the formula I, wherein R6=H and R2, R8 and R9 have above mentioned meanings.

The invention concerns further substituted nitrogen heterocyclic derivatives of the formula I, wherein R2=H and R6, R8 and R9 have above mentioned meanings.

The invention concerns further substituted nitrogen heterocyclic derivatives of the formula Ia,

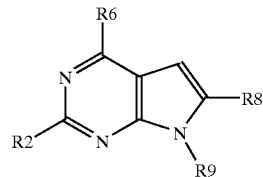

(Ia)

wherein R2, R6, R8 and R9 have above mentioned meanings.

The invention concerns further substituted nitrogen heterocyclic derivatives of the formula Ia, wherein R6=H and R2, R8 and R9 have above mentioned meanings.

The invention concerns further substituted nitrogen heterocyclic derivatives of the formula Ia, wherein R2=H and R6, R8 and R9 have above mentioned meanings.

The invention concerns farther substituted nitrogen heterocyclic derivatives of the formula Ib,

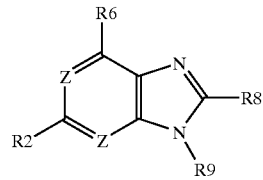

(Ib)

wherein R2, R6, R8 and R9 have above mentioned meanings.

The invention concerns further substituted nitrogen heterocyclic derivatives of the formula Ib, wherein R6=H and R2, R8 and R9 have above mentioned meanings.

The invention concerns further substituted nitrogen heterocyclic derivatives of the formula Ib, wherein R2=H and R6, R8 and R9 have above mentioned meanings.

The invention concerns further substituted nitrogen heterocyclic derivatives of the formula Ic,

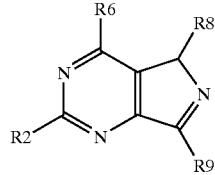

(Ic)

wherein R2, R6, R8 and R9 have above mentioned meanings.

The invention concerns further substituted nitrogen heterocyclic derivatives of the formula Ic, wherein R6=H and R2, R8 and R9 have above mentioned meanings.

The invention concerns further substituted nitrogen heterocyclic derivatives of the formula Ic, wherein R2 =H and R6, R8 and R9 have above mentioned meanings.

The inventions concerns further substituted nitrogen heterocyclic derivatives of the formula Id

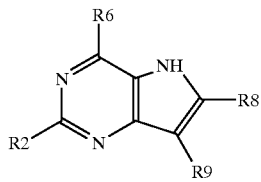

(Id)

wherein R2, R6, R8 and R9 have above mentioned meanings.

The inventions concerns further substituted nitrogen heterocyclic derivatives of the formula Id, wherein R6=H and R2, R8 and R9 have above mentioned meanings.

The invention concerns further substituted nitrogen heterocyclic derivatives of the formula Id, wherein R2=H and R6, R8 and R9 have above mentioned meanings.

The invention concerns further substituted nitrogen heterocyclic derivatives of the formula Ie,

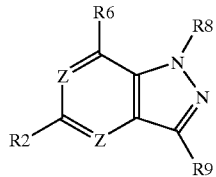

(Ie)

wherein R2, R6, R8 and R9 have above mentioned meanings.

The invention concerns further substituted nitrogen heterocyclic derivatives of the formula Ie, wherein R6=H and R2, R8 and R9 have above mentioned meanings.

The invention concerns further substituted nitrogen heterocyclic derivatives of the formula Ie, wherein R2=H and R6, R8 and R9 have above mentioned meanings. The invention concerns further substituted nitrogen heterocyclic derivatives of the formula If,

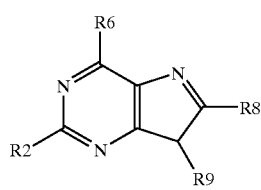

(If)

wherein R2, R6, R8 and R9 have above mentioned meanings.

The invention concerns further substituted nitrogen heterocyclic derivatives of the formula If, wherein R6=H and R2, R8 and R9 have above mentioned meanings.

The invention concerns further substituted nitrogen heterocyclic derivatives of the formula If, wherein R2=H and R6, R8 and R9 have above mentioned meanings.

The invention concerns further substituted nitrogen heterocyclic derivatives of the formula Ig,

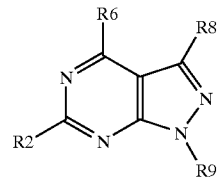

(Ig)

wherein R2, R6, R8 and R9 have above mentioned meanings.

The invention concerns further substituted nitrogen heterocyclic derivatives of the formula Ig, wherein R6=H and R2, R8 and R9 have above mentioned meanings.

The invention concerns further substituted nitrogen heterocyclic derivatives of the formula Ig, wherein R2=H and R6, R8 and R9 have above mentioned meanings.

The invention concerns further substituted nitrogen heterocyclic derivatives of the formula I selected from the group consisting of 2-(1-hydroxymethylpropylamino)-6-benzylamino-8-chloro (or hydroxy, bromo, fluoro, amino, amido, carboxy, cyano, methylamino, thio, methylthio, ω-hydroxyalkylamino, ω-hydroxyalkyloxy, ωcarboxyalkylamino, ωaminoalkylamino, ωfosfonoalkylamino, ω-fosfonoalkyloxy, propinyl)-9-isopropylpurine, 2-(2-aminopropylamino)-6-benzylamino-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-isopropylpurine, 2-(2-hydroxypropylamino)-6-benzylamino-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-isopropylpurine, 2-diethylamino-6-(4-methoxybenzylamino)-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-isopropylpurine, 2-(2-hydroxypropylamino)-6-(3-chloroanilino)-8-chloro (or hydroxy, bromo, amino, $C_1$–$C_6$ alkyl, methyl, ethyl, propyl, isopropyl, vinyl, allyl, propargyl)-9-isopropylpurine, 2-(2-hydroxypropylamino)-6-(3-chloro-4-carboxyanilino)-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-isopropylpurine, 2-(R)-(2-hydroxypyrrolidin-1-yl)-6-benzylamino-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-isopropylpurine, 2-(R)-(1-isopropyl-2-hydroxyethylamino)-6-(3-chloro4-carboxyanilino)-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-isopropylpurine, 2-(R)-(1-isopropyl-2-hydroxyethylamino)-6-benzylamino-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-isopropylpurine, 2-(R)-(1-isopropyl-2-hydroxyethylamino)-6-(3-chloroanilino)-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-isopropylpurine, 2-alkylamino-6-dimethylamino-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-(R)-(2-phosphonomethoxypropyl)purine, 2-alkylamino-6-diethylamino-8-chloro (or hydroxy bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-(R)-(2-phosphonomethoxypropyl)purine, 2-alkylamino-6-butylamino-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-(R)-(2-phosphonomethoxy-propyl)purine, 2-alkylamino-6-(2-butylamino)-8-chloro (or hydroxy, bromo, fluoro, ammo, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-(R)-(2-phosphonomethoxypropyl)purine, 2-alkylamino-6cyclopropylamino-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-(R)-(2-phosphonomethoxypropyl)purine, 2-amino-6-cyclohexylamino-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-(R)-(2-phosphonomethoxypropyl)purine, 2-alkylamino-6-(pyrrolidin-1-yl)-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ω-fosfonoalkylamino, ω-fosfonoalkyloxy, propinyl)-9-(R)-(2-phosphonomethoxypropyl)purine, 2-alkylamino-6-(morpholin-1-yl)-8-chloro (or hydroxy, bromo, fluoro, amino, amido, carboxy, cyano, methylamino, thio, methylthio, ω-hydroxyalkylamino, ω-hydroxyalkyloxy, ω-carboxyalkylamino, ω-aminoalkylamino, ωfosfonoalkylamino, ω-fosfonoalkyloxy, propinyl)-9-(R)-(2-phosphonomethoxypropyl)purine.

The invention also relates to a method for preparing substituted nitrogen heterocyclic derivatives of formula I, wherein R2, R6, R8 and R9 have above mentioned meanings, A is a group of formula.

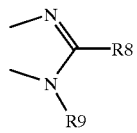

and Z is N, characterized in that a trisubstituted derivative of formula XI, (XI)

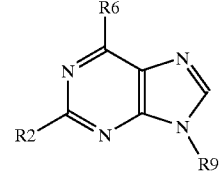

wherein R2, R6 and R9 have above mentioned meanings, is brominated with using a brominating system selected from a group consisting of bromine/acetic acid, bromine/chloroform, bromine/acetate buffer, bromine/water, N-bromosuccinimide/dimethylformamide and bromoacetamide/dimethylformamide to obtain a derivative of formula XIa, (XIa)

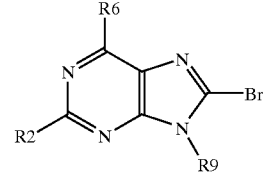

wherein R2, R6 and R9 have above mentioned meanings, and the bromine atom in position 8 of the derivative of formula XIa is then optionally subjected to a substitution in order to replace it by another substituent R8, which has above mentioned meanings.

The invention also relates to a method for preparing substituted nitrogen heterocyclic derivatives of formula I, wherein R2, R6, R8 and R9 have above mentioned meanings, A is a group of formula

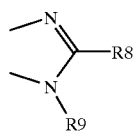

and Z is N, characterized in that a trisubstituted derivative of formula XIb, (XIb)

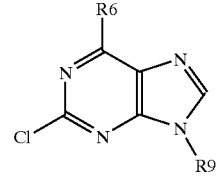

wherein R6 and R9 have above mentioned meanings, is brominated with using a brominating system selected from a group consisting of bromine/acetic acid, bromine/ chloroform, bromine/acetate buffer, bromine/water, N-bromosuccinimide/dimethylformamide and bromoacetamide/dimethylformamide to obtain a derivative of formula XIc,

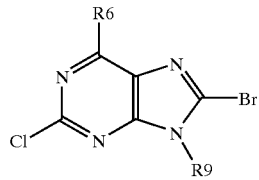

(XIc)

wherein R6 and R9 have above mentioned meanings, and the chlorine atom in position 2 and the bromine atom in position 8 of the derivative of formula XIc are optionally, either progressively or simultaneously, subjected to a nucleophilic substitution in order to replace them by another substituents R2 and R8, that have above mentioned meanings.

The invention also relates to a method for preparing substituted nitrogen heterocyclic derivatives of formula I, wherein R2, R6 and R8 have above mentioned meanings, R9 is alkyl as defined above, A is a group of formula

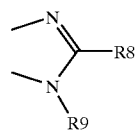

and Z is N, characterized in that, a trisubstituted derivative of formula XIIa,

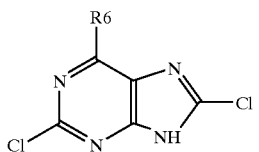

(XIIa)

wherein R6 is as defined above, is alkylated in position 9 with using an appropriate alkylating agent in a system selected from a group consisting of K$_2$CO$_3$/dimethylformamide, Cs$_2$CO$_3$/dimethylformamide, t-BuOK/dimethylformamide, t-BuOK/dimethylsulphoxide and NaH/dimethylformamide or under conditions of Mitsunobu reaction to obtain a derivative of formula XIIb

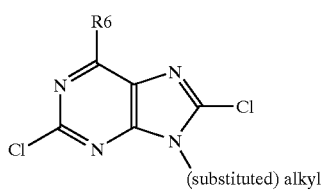

(XIIb)

wherein R6 and alkyl are as defined above, and the chlorine atoms in positions 2 and 8 of the derivative of formula XIIb are optionally, either progressively or simultaneously, subjected to a substitution in order to replace them by another substituents R2 and R8, that have above mentioned meanings.

The invention also relates to a method for preparing substituted nitrogen. heterocyclic derivatives, wherein R2, R6 and R8 have above mentioned meanings, R9 is alkyl as defined above, A is a group of formula

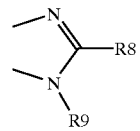

and Z is N, characterized in that a trisubstituted derivative of formula XIIa,

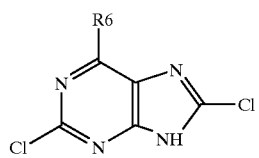

(XIIa)

wherein R6 has above mentioned meanings, is protected by reacting, for example, with 2-dihydropyrane/H$^+$ to obtain a derivative of formula XIIc,

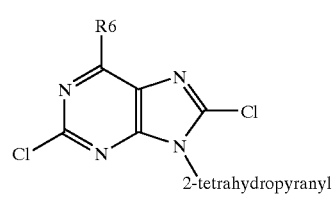

(XIIc)

wherein R6 has above mentioned meanings, and a group R6 and/or the chlorine atom in position 2 and/or the chlorine atom in position 8 are optionally converted to another substituents R2, R6 and R8, that have above mentioned meanings and in such optionally modified product of formula XIIc, the 2-tetrahydropyranyl group is split off to obtain a corresponding derivative of formula XIIc wherein R9 is hydrogen, and so obtained product is then alkylated in position 9 with using an appropriate alkylating agent in a system selected from a group consisting of K$_2$CO$_3$/dimethylformamide, Cs$_2$CO$_3$/dimethylformamide, t-BuOK/dimethylformamide, t-BuOK/dimethylsulphoxide and NaH/dimethylformamide or under conditions of Mitsunobu reaction to obtain a tetrasubstituted derivative of formula XIIc, wherein R2,R6,R8 and R9 have above mentioned meanings.

The invention also relates to a method for preparing substituted nitrogen heterocyclic derivatives of formula I, wherein R2, R6 and R8 have above mentioned meanings, R9 is alkyl as defined above, A is a group

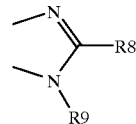

and Z is N, characterized in that, 2,6,8-trichloropurine is subjected to a nucleophilic substitution in position 6 in order to replace the chlorine atom in position 6 by another substituent R6 as defined above to obtain a derivative of formula XIIa,

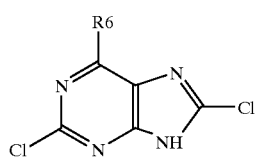

(XIIa)

wherein R6 has above mentioned meanings, and so obtained product is then alkylated in position 9 with using an appropriate alkylating agent in a system selected from a group consisting of K₂CO₃/dimethylformamide, Cs₂CO₃/dimethylformamide, t-BuOK/dimethylformamide, t-BuOK/dimethylsulphoxide and NaH/dimethylformamide or under conditions of Mitsunobu reaction to obtain a derivative of formula XIIb,

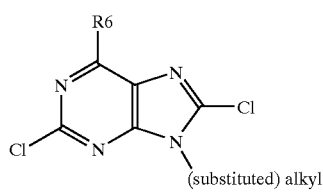

(XIIb)

wherein R6 and alkyl have above mentioned meanings, and the chlorine atoms in positions 2 and 8 of the derivative of formula XIIb are optionally, either progressively or simultaneously, subjected to a nucleophilic substitution in order to replace them by another substituents R2 and R8 that have above mentioned meanings.

The invention also relates to a method for preparing substituted nitrogen heterocyclic derivatives of formula I, wherein R2 is hydrogen, R6 and R8 have above mentioned meanings, R9 is alkyl as defined above, A is a group of formula

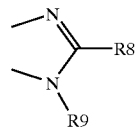

and Z is N, characterized in that 6,8-dichloropurine is subjected to a substitution in position 6 in order to replace the chlorine atom in position 6 by another substituent R6 which has above mentioned meanings to obtain a derivative of formula XVI,

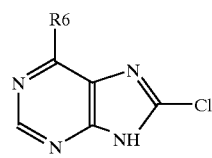

(XVI)

wherein R6 has above mentioned meanings, and so obtained derivative is alkylated in position 9 with using an appropriate alkylating agent in a system selected from a group consisting of K₂CO₃/dimethylformamide, Cs₂CO₃/dimethylformamide, t-BuOK/dimethylformamide, t-BuOK/dimethylsulphoxide and NaH/dimethylformamide or under conditions of Mitsunobu reaction to obtain a derivative of formula XVIa,

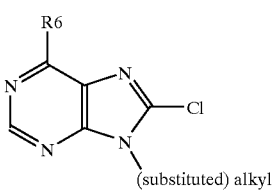

(XVIa)

wherein R6 and alkyl have above mentioned meanings, and the chlorine atom in position 8 of the derivative of formula XVIa is optionally subjected to a substitution in order to replace it by another substituent R8 which has above mentioned meanings.

The invention also relates to a method for preparing substituted nitrogen heterocyclic derivatives of formula I, wherein R2, R6 and R8 have above mentioned meanings, R9 is alkyl as defined above, A is a group of formula

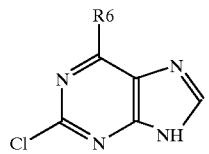

and Z is N, characterized in that 2,6-dichloropurine is subjected to a nucleophilic substitution in position 6 in order to replace the chlorine atom in position 6 by another substituent R6 as defined above, and so obtained derivative of formula XVII, (XVII)

wherein R6 is as defined above, is alkylated in position 9 with using either methyl acrylate or acrylonitrile or oxirane to obtain a derivative of formula XVIIa

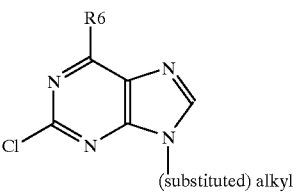

(XVIIa)

wherein R6 and alkyl have above mentioned meanings, which product is then brominated in position 8 with using a brominating system selected from a group consisting of bromine/acetic acid, bromine/chloroform, bromine/acetate buffer, bromine/water, N-bromosuccinimide/dimethylformamide and bromoacetamide/dimethylformamide to obtain a derivative of formula XVIIb,

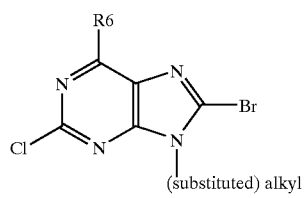

(XVIIb)

wherein R6 and alkyl have above mentioned meanings, and so obtained product is then optionally, either progressively or simultaneously, subjected to a nucleophilic substitution in positions 2 and 8 in order to replace the chlorine atom in position 2 and the bromine atom in position 8 by another substituents R2 and R8 that have above mentioned meanings.

The invention also relates to a method for preparing substituted nitrogen heterocyclic derivatives of formula I, wherein R6 is a halogen or hydrogen, R2, R8 and R9 have above mentioned meanings, A is a group of formula

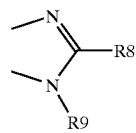

and Z is N, characterized in that a derivative of formula XVIII,

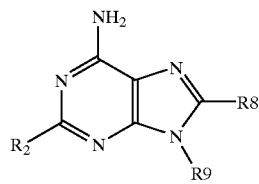

(XVIII)

wherein R2, R8 and R9 have above mentioned meanings, is halogenated via diazotation with using, for example, amylnitrite/$CH_2Br_2$ or amylnitrite/$CHI_3$, and so obtained derivative wherein R6 is halogen is optionally hydrogenolyzed with using $H_2$/Pd catalyst to obtain a corresponding derivative wherein R6 is hydrogen.

The invention also relates to a method for preparing substituted nitrogen heterocyclic derivatives of formula I, wherein R9 has above mentioned meanings and one substituent of R2, R6 or R8 is alkinyl or alkenyl containing 1 to 6 carbon atoms whereas two other substituents of R2, R6 and R8 have above mentioned meanings, A is a group of formula

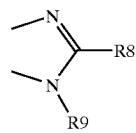

and Z is N or CH, characterized in that a derivative of formula I, wherein R9 has above mentioned meanings and one substituent of R2, R6 and R8 is a halogen whereas two other substituents of R2, R6 and R8 have above mentioned meanings, is alkinylated in the position of the halogen with using alkine/triphenylphosphine-$PdCl_2$/CuI/triethylamine system and so obtained 2-, 6- or 8-alkinyl derivative is optionally converted to 2-, 6- or 8-alkenyl derivative with using a Lindlar catalyst.

The invention also relates to a method for preparing substituted nitrogen heterocyclic derivatives of formula I, wherein R2, R6, R8 and R9 have above mentioned meanings, A is a group of formula

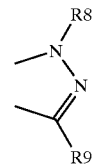

and Z is N, characterized in that 2,5-dialkyl-3-alkoxykarbonyl-4-aminopyrazole, wherein alkyls and alkoxy have above mentioned meanings, is reacted with formamidine acetate/triethylamine system to obtain 1,3-dialkyl-7-hydroxypyrazolo[4,3-d]pyrimidine and so obtained 7-hydroxy derivative is then optionally transferred to a corresponding 7-chloro derivative by reaction with thionylchloride, which product is optionally substituted to obtain a corresponding R6-derivative, wherein R6 has above mentioned meanings.

The invention also relates to a method for preparing substituted nitrogen heterocyclic derivatives of formula I, wherein R2, R6, R8 and R9 have above mentioned meanings, A is a group of formula

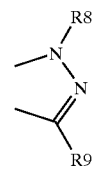

and Z is N, characterized in that 3,7-dialkylpyrazolo[4,3-d]pyrimidine, wherein alkyls have above mentioned meanings, is alkylated with using an appropriates alkylating agent in a system selected from a group consisting of $K_2CO_3$/dimethylformamide and $Cs_2CO_3$/dimethylformamide to obtain a mixture of trialkylated and tetraalkylated products and the trialkylated product is separated by means of the column chromatography.

The invention also relates to substituted nitrogen heterocyclic derivatives of formula I and pharmaceutically acceptable salts thereof for use as medicaments.

The invention also relates to substituted nitrogen heterocyclic derivatives of formula I for use as means for preparing affinity adsorption matrices, immobilized enzymes for process control, immunoassay reagents, diagnostic samples, $^{14}C$—, $^3H$—, avidin- or biotin-labelled compounds, oligonucleotides and diagnostic samples.

The invention also relates to substituted nitrogen heterocyclic derivatives of formula I for use as antimitotic drugs, in particular drugs for elimination or reduction of viral spread or growth in tissue culture systems during the production of biopharmaceutical or other products such as proteins and vaccines, drugs for elimination or reduction of viral spread and growth in clinical samples such as blood, and drugs for stopping of growth of tissue culture cells while leaving the cells to carry on with protein production.

The invention also relates to a pharmaceutical composition with cytostatic, anticancer, antimitotic, antineurodegenerative, inmunosuppressive and antimicrobial activity, characterised in that it comprises, in addition to auxiliary pharmaceutical matters, at least one substituted nitrogen heterocyclic derivative of formula I.

The invention also relates to a combined pharmaceutical composition with cytostatic effect, characterised in that it comprises, in addition to auxiliary pharmaceutical matters, a combination of at least one substituted nitrogen heterocyclic derivative of formula I and a cytostatic agent selected from a group consisting of mitoxantron, cis- and carbo-platin, methotrexate, taxol and doxorubicin.

The invention also relates to a use of substituted nitrogen heterocyclic derivatives of formula I for preparing medicaments destined for treating tumours, cancers, psoriasis, rheumatoid arthritis, lupus, type I diabetes, multiple sclerosis, restenosis, polycyclic kidney disease, host graft disease and gout, parasitoses, such as those caused by fungi or prostis, or Alzheimer's disease, or for preparing antineurodegenerative drugs and suppress immunostimulation agents.

The novel compounds of this invention have a wide variety of diagnostic, therapeutic and industrial utilities.

The compounds of this invention are suitable as intermediates for use in the preparation of affinity absorption matrices. For example, the phosphonate groups in matrix bound form are useful in the chromatographic separation of positively charged molecules. Other immobilised examples of the compounds herein are useful in purifying proteins, e.g., cell cycle enzymes (cdk's), enzymes involved in recognition of the compound of this invention, e.g. transport proteins. Suitable methods of incorporation of the compounds of this invention into polymeric resins will be readily apparent to the skilled artisan, for instance the compounds are incorporated by cross-linking hydroxyl groups of the phosphonate or hydroxymethyl substituents using cross-linking agents heretofore known. Linking through a group other than the heterocyclic base will produce a resin useful in hydrophobic affinity chromatography. Other suitable linking methods are described in Cihlar (supra).

The compounds of the formula I and their pharmaceutically acceptable salts inhibit selectively the enzyme $p34^{cdc2}$/cyclin-B kinase and related cdks (cdk2, cdk5, cdk7, erk1, erk2).

In another embodiment, this invention is a method for inhibiting cdks and cell proliferation in mammals comprising administering a therapeutically effective amount of the composition of claim 1 to the mammal. The cdk inhibiting molecules are useful for treating cell proliferation disorders such as rheumatoid arthritis, lupus, type I diabetes, multiple sclerosis, cancer, restenosis, Alzheimer's disease, growth of parasites (animal, protists), host graft disease, and gout.

In another embodiment, this invention is a composition useful for treating fungal infections (fungi) in humans, animal, and in plants.

2,6,9,9-Tetrasubstituted and 6,8,9- or 2,8,9-trisubstituted adenine derivatives exhibit extremely high potency against DNA viruses on the part of the defined compounds. Such compounds otherwise have been considered to have little or no activity against DNA viruses. Moreover, surprisingly the chirally enriched or pure (S)-enantiomer is antivirally active. Heretofore, only the (R)-enantiomer was notably antivirally active, and then only against retroviruses.

In addition to other cdc2-related kinases, this kinase controls certain steps of cell division cycles, in particular the transition from G1 phase into the S phase and in particular the transition from the G2 phase into the M phase. Out the basis of this findings, it can be expected that the compounds of the formula I, II and their pharmaceutically acceptable salts can be used as antimitotic compounds or for treatment of hypoproliferative diseases, such as cancer, restenosis and Alzheimer's disease. Thus in very low concentration (micromolar and lower), they are capable of inhibiting cell cycle transitions,(G1/S, G2/M, M-phase/metaphase) carried out on the different animal bodies and embryos. Furthermore, the compounds are useful in treating autoimune diseases, e.g. rheumatoidal arthritis, lupus, type I diabetes, multiple sclerosis, etc., in treating of cancer, cardiovascular disease such as restenosis, host vs graft disease, gout, polycystic kidney disease and other proliferative diseases whose pathogenesis involves abnormal cell proliferation.

This invention also concerns novel compounds that have been discovered to be potent and specific inhibitors of I$\kappa$B-$\alpha$ kinase which prevents signal induced NF-$\kappa$B activation and cytokine synthesis in vitro and in vivo. Such inhibitors are expected to inhibit synthesis of cytokines and adhesion proteins whose synthesis is transcriptionally regulated by NF-$\kappa$B. Pro-inflammatory cytokines such as IL-1, IL-6, TNF and adhesion proteins (e.g. ICAM, VCAM and selections) belong to this class of molecules and have implicated in the pathogenesis of inflammatory diseases. Thus a potent inhibitor of I$\kappa$B-$\alpha$ kinase is useful in the clinical management of diseases where the NF-$\kappa$B activation is required for disease induction.

It also relates to novel compounds activating p53, the mammal cell's own natural brake gene for stopping uncontrolled cell proliferation (cancer), thus being able to switch off the cancer. p53 as well as retinoblastoma (Rb) are two well-characterised tumour suppressors whose inactivation may led to uncontrolled cell proliferation and malignancy. Phosphorylation of these two proteins, which are involved in the cell cycle regulatory mechanisms, is known to modulate their function. Thus a potent cdk inhibitor represent a good toll for treatment of cancers due to induction of wild type p53 protein in cancers expressing mutant p53.

In addition, studies carried out on the derivatives of the invention have demonstrated strong effect on apoptosis of many cancer cell lines. It has been seen that apoptosis can be induced at stage G1 or G2 and following damage of the DNA, some cells stop at stage G1 and p53-dependent apoptotic pathway is then induced. In other situations, it seems that cells stop at G2/M stage in response to damage caused to the DNA, and activation of an independent p53 apoptotic path is observed. This path has proved to be particularly significant in the therapy of tumours in which a less of active p53 is observed. The interest is therefore assessed by application of the derivatives of the invention for stimulating on of p53-independent apoptosis in the cells, which have stopped at stage G2 through damage to the DNA using agents such as mitoxantrone or cis-platinum. The cdk inhibitors of this invention can thus increase the therapeutic potential of the anti-tumour agents currently used.

The compounds of this invention will generally be terminally incorporated into the oligonucleotide. If they do not contain phosphonyl group attached to the hydroxyl group, they optionally are incorporated internally into the sequence of the oligonucleotide. Terminally incorporated diphosphonyl compounds of this invention which contain no free hydroxyl capable of participating in chain elongation also are useful in DNA sequencing in essentially the same manner as deoxyNTPs have been used in the past (see example 8 of U.S. Pat. No. 5,276,143). The nucleotide analogues of the invention (when diphosphorylated) are useful as chain terminators for dideoxynucleotide-type DNA sequencing protocols, provided that the nucleotide analogue lacks a free hydroxyl group suitable for polymerase mediated chain elongation. These compounds will not have R=hydroxymethyl and do not posses a cyclic structure incorporating the phosphorus atom (although compounds having such excluded structures can be intermediates). The nucleotide analogue is included in a kit with other reagents (such as Klenow polymerase or T4 polymerase, dNTPs, etc) needed for DNA sequencing (Otvos, et al. "Nucl. Acids.Res."15:1763–1777 (1987).

If the oligonucleotide-incorporated compound of this invention is binding-competent for its complementary sequence, i.e., if it is capable of base pairing, then this nucleotide monomer will participate in hybridisation. It is not necessary, however, that the incorporated nucleotide analogue of this invention base pair or otherwise participate in hybridisation. If it is located at the terminus of the oligonucleotide it will be useful as an immunological recognition site, or haptenic recognition site, to facilitate detection of the oligonucleotide by an antibody capable of binding the compound of this invention.

The compounds of this invention also are useful as linkers or spacers in preparation affinity absorption matrices (as opposed to functioning as affinity moieties per se as noted above), immobilised enzymes for process control, or immunoassay reagents. The compounds herein contain a multiplicity of functional groups that are suitable as sites for cross-linking desired substances. For example, it is conventional to link affinity reagents such as hormones, peptides, antibodies, drugs, and the like to insoluble substrates. These insolubilised reagents are employed in known fashion to absorb binding partners for the affinity reagents from manufactured preparations, diagnostic samples and other impure mixture. Similarly, immobilised enzymes are used to perform catalytic conversions with facile recovery of enzyme. Bifunctional compounds are commonly used to link analytes to detectable groups in preparing diagnostic reagents.

Many functional groups present in the compounds of this invention are suitable for use in cross-linking. For example, the phosphonic acid is used to form esters with alcohols or amides with amines. The R groups substituted with OH, azido (which is reduced to amino if desired before cross-linking) or vinyl are exemplary suitable sites. Similarly, the amino, halo, acyl and other reactive sites found on group B are suitable. Suitable protection of reactive groups will be used where necessary while assembling the cross-linked reagent. In general, the compounds here are used by linking them through phosphonic acid or amino group to the hydroxyl or amino groups of the linking partner in the same fashion as shown herein, and covalently bonded to the other binding partner through an R group. For example a first binding partner such as a steroid hormone is esterified and then this conjugate is cross-linked through hydroxymethyl R to cyanogen bromide activated Sepharose, whereby immobilised steroid is obtained. Other chemistries for conjugation are well known. See for example Maggio, "Enzyme-Immunoassay" (CRC, 1988, pp 71–135) and references cited therein.

The oligonucleotides of this invention are labelled with any conventional detectable label, e.g. a fluorescent moiety such a fluorescein, radioisotopes such as $^{14}C$ or $^{3}H$, stable free radicals, avidin, biotin and the like all of which previously have been used as labels for immunoassays or diagnostic probes. The label will be present on the oligonucleotide or on the residue of an analogue of this invention. Suitable labelling methods are well known and are readily used with reactive groups such as hydroxyl, allyl and the like. A simple method is to label the compound of this invention with $H_3$ by proton exchange. The compounds also are biotinylated using conventional methods. See for instance U.S. Pat. No. 5,276,143 for analogous structures. However, the compounds of this invention also are useful directly in diagnostic probe assays without an exogenous detectable label. In one embodiment of this alternative, antibodies are raised against the compounds of this invention. Such antibodies (which in turn are labelled or used in a double antibody configuration) bind to the analogue of this invention and thereby are useful in detecting its presence as label for a protein or oligonucleotide.

The compounds of the invention are useful for treatment of microbial infections, for treatment of tumours or for other indications described below. Microbial infections treatable by the compounds of this invention include viruses, parasites, yeast and fungi, but it is believed that the compounds are most effective against viruses, which constitutes the preferred utility. Exemplary viral infections include infections caused by DNA or RNA viruses including herpes viruses (CMV, HSV 1, HSV 2, EBV, varicella zoster virus (VZV), bovid herpesvirus type 1, equid herpesvirus type 1, HVV-6, papillomaviruses (HPV types 1–55 including carcinogenic HPV), flaviviruses (including yellow fever virus, African swine fever virus and Japanese encephalitis virus), togaviruses (including Venezuelan equine encephalomyelitis virus), influenza viruses (types A–C), retroviruses (HIV-1, HIV-2, HTLV-I, HTLV-II, SIV, FeLV, FIV, MoMSV), adenoviruses (types 1–8), poxviruses (vaccinia virus), enteroviruses (poliovirus types 1–3, Coxsackie, hepatitis A virus, and ECHO virus), gastroenteritis viruses (Norwalk viruses, rotaviruses), hantaviruses (Hantaan virus), polyomavirus, papovaviruses, rhinoviruses, parainfluenza virus types 1–4, rabies virus, respiratory synctial virus (RSV), hepatitis viruses A, B, C and E, and the like.

The antiviral activity of individual compounds is determined by routine assay of antiviral (or other antimicrobial) activity using enzyme inhibition assays, tissue culture assays, animal model assays and the like as will be understood by those skilled in the art.

Protozoan parasite infections are treated using the compounds of the invention. The term protozoa include those members of the subphyla Sarcomastigophora and Sporozoa of the phylum Protozoa. More particularly, the term protozoa as used herein include genera of parasitic protozoa, which are important to man, because they either cause disease in man or in his domestic animals. These genera for the most part are classified in the superclass Mastigophora of the subphylum Sarcomastigophora and the class Telesporea of the subphylum Sporozoa in the classification according to Baker (1969). Illustrative genera of these parasitic protozoa include Histomonas, Pneumocystis, Trypanosoma, Giardia, Trichomonas, Eimeria, Isopora, Leishmania, Entamoeba, Toxoplasma and Plasmodium. Parasitic protozoans include *Plasmodium falciparum, Plasmodium berghei, Plasmodium malariae, Plasmodium vivax, Leishmania braziliensis, Leishmania donovani, Trypanosoma cruzi, Trypanosoma brucei, Trypanosoma rhodesiense, Pneumocystis carinii, Entamoeba histolytica, Trichomonas vaginal* and the like (de Vries, E., et al, "Mol. Biochem. Parasitol" 47:43–50 (1991) and trypanosomes (Kaminsky et al. "J.Parasitol." 80(6): 1026-30 (1994). The compounds in which R is $CH_2OH$ and B is 3-deazaadenine are particularly interesting in the treatment of malarial parasites.

Compounds of the invention are used to treat yeast or fungal infections caused by *Candida glabrata, Candida ropicalis, Candida albicans,* and other Candida species, Crypococcus species including *Cryptococcus neoformans,* Blastomyces species including *Blastomyces dermatidis,*

Torulopsis species including *Torulopsis glabrata*, Coccidioides species including *Coccidioides immitis*, Aspergillus species and the like.

The compounds of the invention can also be (1) applied to tissue culture systems to eliminate or reduce viral spread or growth during the production of biopharmaceutical or other products (such as proteins or vaccines), (2) used to eliminate or reduce viral spread or growth in clinical sample (such as blood), and (3) used to stop growth of tissue culture cells while leaving the cells to carry on with protein production.

The compounds herein have been found to suppress inmmunostimulation. Accordingly, they can suppress metabolic activities of T-lymphocytes stimulated by diverse agents, e.g. concavalin A, they principally will find application in the treatment of autoimmune diseases, e.g. arthritis, or in suppression of transplant rejection. Their therapeutically active concentrations are in the range of 1 mg/kg to 50 mg/kg of body weight.

Therapeutic Administration

Suitable routes for administration include oral, rectal, vassal, topical (including ocular, buccal and sublingual), vaginal and parental (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutical composition comprise about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of convential mixing, granulating, coating, dissolving or lyophilising processes.

Preferably, solutions of the active ingredient, and in addition also suspensions or dispersions, especially isotonic aqueous solutions, dispersions or suspensions, are used, it being possible for these to be prepared before use, for example in the case of lyophilised compositions which comprise the active substance by itself or together with a carrier, for example mannitol. The pharmaceutical compositions can be sterilised and/or comprise excipients, for example preservatives, stabilisers, wetting agents and/or emulsifiers, solubilizing agents, salts for regulating the osmotic pressure and/or buffers, and they are prepared in a manner known per se, for example by means of convential dissolving or lyophilising processes. The solutions or suspensions mentioned can comprise viscosity-increasing substances, such as sodium carboxymethylcellulose, carboxymethylcellulose, dextran, polyvinylpyrrolidone or gelatin.

Suspensions in oil comprise, as the oily component, the vegetable, synthetic or semisynthetic oils customary for injection purposes. Oils which may be mentioned are, in particular, liquid fatty acid esters which contain, as the acid component, a long-chain fatty acid having 8–22, in particular 12–22, carbon atoms, for example lauric acid, tridecylic acid, myristic acid, pentadecylic acid, palmitic acid, margaric acid, stearic acid, arachidinic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris) and/or "Miglyol 812" (triglyceride of saturated fatty acids of chain length $C_8$ to $C_{12}$ from Hüls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol cellulose preparations and/or calcium phosphates, for example tricalcium phosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinyl-pyrrolidine, and/or, if desired, desintegrators, such as the above mentioned starches, and furthermore carboxymethyl-starch, crosslinked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, are also hard capsules of gelatin and soft, closed capsules of gelatin and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, parrafin oil or liquid polyethylene glycols or fatty acid esters of ethylene glycol or propylene glycol, it being likewise possible to add stabilisers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parenteral administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilisers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example. Antioxidants, such as ascorbic acid, or microbicides, such as sorbic or benzoic acid.

Ointments are oil-in-water emulsions, which comprise not more than 70%, but preferably 20–50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also contain emulsifiers and/or additives mentioned in connection with the ointments which increase uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding nonionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminium silicates, which have the task of binding the moisture or secretions present.

Foams are administered from pressurised containers and they are liquid oil-in-water emulsions present in aerosol for. As the propellant gases, halogenated hydrocarbons, such as chlorofluoro-lower alkanes, for example dichlorofluoromethane and dichlorotetrafluoroethane, or, preferably, non-halogenated gaseous hydrocarbons, air, $N_2O$, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives, are admixed.

The present invention further provides veterinary compositions comprising at least one active ingredient as above defined together with a veterinary carrier therefor. Veterinary carriers are materials for administering the composition and may be solid, liquid or gaseous materials, which are inert or acceptable in the veterinary art and are compatible with the active ingredient. These veterinary compositions may be administered orally, parenterally or by any other desired route.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

EXAMPLES OF THE INVENTION

Example 1

2-(3-hydroxypropylamino)-6-benzylamino-8-bromo-9-isopropylpurine. 1 mmol of 2-(3-hydroxypropylamino)-6- benzylamino-9-isopropylpurine was dissolved in chloroform and 1.1 mmol of bromine was added. The 8-bromo derivative hydrobromide was removed by filtration and crystallized from n-propanol-ether. M.p. 156–161° C. Yield 90%. TLC: chloroform-methanol (96:4), single spot. MS-ESI(+)m/z: 420, 422 [M+H]$^+$

TABLE 1

Compounds Prepared by the Method of Example 1

SUBSTITUENT

| C2 | N6 | C8 | N9 |
|---|---|---|---|
| 2-hydroxyethylamino | benzylamino | bromo | methyl |
| 3-hydroxypropylamino | benzylamino | bromo | isopropyl |
| (R)-1-(hydroxymethyl)-propylamino | benzylamino | bromo | isopropyl |
| (R)-1-(hydroxymethyl)-propylamino | 3-iodobenzylamino | bromo | isopropyl |
| diethanolamino | 3-chloroanilino | bromo | isopropyl |
| (R)-1-(hydroxymethyl)-isobutylamino | 4-methoxybenzylamino | bromo | isopropyl |
| (R)-1-(hydroxymethyl)-isobutylamino | 3-chloroanilino | bromo | isopropyl |

Example 2

2-(3-hydroxypropylamino)-6-benzylamino-8-methylthio-9-isopropylpurine. 2-(3-Hydroxypropylamino)-6-benzylamino-8-bromo-9-isopropylpurine (0.15 mmol), prepared as described in Example 1, was dissolved in 2 mL dimethylformamide, 0.9 mmol of CH$_3$SNa was added and the mixture stirred at 40° C. for 1 hour. The solvent was removed in vacuo and the rest partitioned between water-EtOAc. The organic layer was dried, evaporated and the rest purified by column chromatography (silica gel, chloroform-heptane (8:2)). Yield 75%. M.p. 64–67° C.

$^1$H NMR (300 MHz, CDCl$_3$): 7.28–740 m, 5.55 t, 4.85 t, 4.75 d, 4.65 m, 3.62 m, 2.62 s, 174 dd, 1.60 d. MS-ESI(+) m/z: 387 [M+H]$^+$

TABLE 2

Compounds Prepared by the Method of Example 2

SUBSTITUENT

| C2 | N6 | C8 | N9 |
|---|---|---|---|
| 2-hydroxyethyl-amino | benzylamino | methyl | methyl |
| 2-hydroxyethyl-amino | benzylamino | mercapto | methyl |
| 2-hydroxyethyl-amino | benzylamino | hydroxy | methyl |
| 2-hydroxyethyl-amino | benzylamino | amino | methyl |
| 2-hydroxyethyl-amino | benzylamino | 2-hydroxyethyl-amino | methyl |
| 2-hydroxyethyl-amino | benzylamino | aminomethyl-amino | methyl |
| 3-hydroxypropyl-amino | benzylamino | methyl | isopropyl |
| 3-hydroxypropyl-amino | benzylamino | mercapto | isopropyl |
| 3-hydroxypropyl-amino | benzylamino | hydroxy | isopropyl |
| 3-hydroxypropyl-amino | benzylamino | amino | isopropyl |
| 3-hydroxypropyl-amino | benzylamino | 2-hydroxyethyl-amino | isopropyl |
| 3-hydroxypropyl-amino | benzylamino | aminomethyl-amino | isopropyl |
| (R)-1-(hydroxy-methyl)propylamino | benzylamino | methyl | isopropyl |
| (R)-1-(hydroxy-methyl)propylamino | benzylamino | mercapto | isopropyl |
| (R)-1-(hydroxy-methyl)propylamino | benzylamino | hydroxy | isopropyl |
| (R)-1-(hydroxy-methyl)propylamino | benzylamino | amino | isopropyl |
| (R)-1-(hydroxy-methyl)propylamino | benzylamino | 2-hydroxyethyl-amino | isopropyl |
| (R)-1-(hydroxy-methyl)propylamino | benzylamino | aminomethyl-amino | isopropyl |
| (R)-1-(hydroxy-methyl)propylamino | 3-iodobenzylamino | methyl | isopropyl |
| (R)-1-(hydroxy-methyl)propylamino | 3-iodobenzylamino | mercapto | isopropyl |
| (R)-1-(hydroxy-methyl)propylamino | 3-iodobenzylamino | hydroxy | isopropyl |
| (R)-1-(hydroxy-methyl)propylamino | 3-iodobenzylamino | amino | isopropyl |
| (R)-1-(hydroxy-methyl)propylamino | 3-iodobenzylamino | 2-hydroxyethyl-amino | isopropyl |
| (R)-1-(hydroxy-methyl)propylamino | 3-iodobenzylamino | aminomethyl-amino | isopropyl |
| diethanolamino | 3-chloroanilino | methyl | isopropyl |
| diethanolamino | 3-chloroanilino | mercapto | isopropyl |
| diethanolamino | 3-chloroanilino | hydroxy | isopropyl |
| diethanolamino | 3-chloroanilino | amino | isopropyl |
| diethanolamino | 3-chloroanilino | 2-hydroxyethyl-amino | isopropyl |
| diethanolamino | 3-chloroanilino | aminomethyl-amino | isopropyl |
| (R)-1-(hydroxy-methyl)isobutyl-amino | 4-methoxybenzyl-amino | mercapto | isopropyl |
| (R)-1-(hydroxy-methyl)isobutyl-amino | 4-methoxybenzyl-amino | hydroxy | isopropyl |
| (R)-1-(hydroxy-methyl)isobutyl-amino | 4-methoxybenzyl-amino | amino | isopropyl |
| (R)-1-(hydroxy-methyl)isobutyl-amino | 4-methoxybenzyl-amino | 2-hydroxyethyl-amino | isopropyl |
| (R)-1-(hydroxy-methyl)isobutyl-amino | 4-methoxybenzyl-amino | aminomethyl-amino | isopropyl |
| (R)-1-(hydroxy-methyl)isobutyl-amino | 3-chloroanilino | methyl | isopropyl |
| (R)-1-(hydroxy-methyl)isobutyl-amino | 3-chloroanilino | mercapto | isopropyl |
| (R)-1-(hydroxy-methyl)isobutyl-amino | 3-chloroanilino | hydroxy | isopropyl |
| (R)-1-(hydroxy-methyl)isobutyl-amino | 3-chloroanilino | amino | isopropyl |
| (R)-1-(hydroxy-methyl)isobutyl-amino | 3-chloroanilino | 2-hydroxyethyl-amino | isopropyl |
| (R)-1-(hydroxy-methyl)isobutyl-amino | 3-chloroanilino | aminomethyl-amino | isopropyl |

Example 3

6-(3-Methoxybenzylamino)-2-chloro-8-bromo-9-isopropylpurine. 1 mmol of 6-(3-methoxybenzylamino)-2-chloro-9-isopropylpurine was brominated with 1.1 mmol of bromine as described in Example 1. The crude 2,8-dihalogeno derivative prepared was alkalinized with $NH_3$/MeOH and extacted between water-EtOAc. The product crystallizes after partial evaporation of ethylacetate. M.p.123–125° C., yield 88%. MS-ESI(+)m/z 409.5, 411.4, 413.3 [M+H]$^+$ Example 4

6-Phenylamino-2-(3-aminopropylamino)-9-isopropyl-8-aminopurine. 6-Phenylamino-2-(3-aminopropylamino)-9-isopropyl-9-benzylaminopurine, prepared from appropriate 8-bromo derivative, was dissolved in glacial acetic acid. To this solution, 50 mg Pd/BaSO$_4$ (10%) was added and the mixture hydrogenated to constant consumption of hydrogen (2 hours). The catalyst was removed by centrifugation and acetic acid was evaporated in vacua. The rest was purified by column chromatography (silica gel, chloroform-MeOH-conc. NH$_4$OH (95:5:1). Yield 75%. MS-ESI(+)m/z 340.5 [M+H]$^+$ Example 5

6-(4-Methoxybenzylamino)-2,8-bis(3-hydroxypropylamino)-9-isopropylpurine. 6-(4-Methoxybenzylamino)-2,8-bis(3-hydroxypropylamino) purine (0.07 mmol) was stirred in 2 mL dimethylformamide with 0.14 mmol of allylbromide and with 0.36 mmol of dry potassium carbonate at ambient temperature (6 hours). The solvent was evaporated to dryness and the rest extracted between ethylacetate—water. The organic layer was dried, ethylacetate was evaporated and the rest purified by column chromatograpy (silica gel, chloroform). Yield 55%. MS-ESI (+)m/z 441.4 [M+H]$^+$

TABLE 3

Compounds Prepared by the Method of Example 5

| | SUBSTITUENT | | |
|---|---|---|---|
| C2 | N6 | C8 | N9 |
| 2-hydroxyethyl-amino | benzylamino | 2-hydroxyethyl-amino | allyl |
| 3-hydroxypropyl-amino | 4-methoxybenzyl-amino | 3-hydroxypropyl-amino | allyl |
| 2-aminoethylamino | benzylamino | 2-aminoethylamino | isopropyl |
| 3-aminopropyl-amino | benzylamino | 3-aminopropyl-amino | isopropyl |
| aminomethylamino | benzylamino | aminomethylamino | isopropyl |
| diethanolamino | benzylamino | diethanolamino | isopropyl |
| hydroxymethyl-amino | benzylamino | hydroxymethyl-amino | isopropyl |
| 3-aminopropyl-amino | benzylamino | 3-aminopropyl-amino | isopropyl |
| 2-hydroxyethyl-amino | 3-chloroanilino | 2-hydroxyethyl-amino | isopropyl |
| 3-hydroxypropyl-amino | 3-chloroanilino | 3-hydroxypropyl-amino | isopropyl |
| 2-aminoethylamino | 3-chloroanilino | 2-aminoethylamino | isopropyl |
| 3-aminopropyl-amino | 3-chloroanilino | 3-aminopropyl-amino | isopropyl |
| diethanolamino | benzylamino | diethanolamino | isopropyl |
| hydroxymethyl-amino | benzylamino | hydroxymethyl-amino | isopropyl |
| (R)-1-(hydroxy-methyl)isobutyl-amino | 3-chloroanilino | (R)-1-(hydroxy-methyl)isobutyl-amino | isopropyl |

Example 6

6-Benzylamino-8-hydroxyethylamino-9-isopropylpurine. 1 mmol of 6-chloropurine was alkylated with isopropylbromide in DMF as described in Example 5. The product, 6-chloro-9-isopropylpurine was brominated in acetic acid similarly as described in Example 1. After purification by column chromatography, 6-benzylamino-9-isopropyl-8-bromopurine was treated with 2-aminoethanol to give 6-benzylamino-8-hydroxyethylamino-9-isopropylpurine. Yield 40%. MS-ESI(+)m/z 326 [M+H]$^+$ Example 7

2-(3-Hydroxypropylamino)-9-methyl-8-(3-hydroxypropyloxy)purine. 6-Amino-2-(3-hydroxypropylamino)-9-methyl-8-(3-hydroxypropyloxy) purine was brominated in the position 6 with amylnitrite/CH$_2$Br$_2$. The 6-bromo derivative was then hydrogenolyzed with PdO/BaSO$_4$ in strong alkaline solution to give 2,8,9-trisubstituted purine. The crude product was purified by column chromatography (silica gel, chloroform-MeOH-conc. NH$_4$OH (8:2:0.2)). The total yield was 35%. MS-ESI (+)281 [M+H]$^+$ Example 8

7-Hydroxy-1-methyl-3-isopropylpyrazolo[4,3]pyrimidine. 0.02 mmol of 2-Methyl4-amino-3-alkoxycarbonyl-5-isopropylpyrazole (prepared from appropriate 4-nitro derivative by catalytic hydrogenation) was dissolved in 30 mL of 2-ethoxyethanol and 0.02 mmol of formamidin acetate and 5.2 mL of triethylamine were added. The mixture was heated to 90° C. for 2 hours. The solution was concentated in vacuo, dissolved in chloroform to give crystalline product. After recrystallization from ethanol m.p. 295–298° C. MS-ESI(+)m/z 193 [M+H]$^+$ Example 9

7-(2-Hydroxybenzylamino)-1-methyl-3-isopropylpyrazolo[4,3]pyrimidine. 1.1 mmol of 7-Hydroxy-1-methyl-3-isopropylpyrazolo[4,3]pyrimidine (Example 8) was dissolved in the mixture of 0.12 mL of dimethylformamide and 5 mL dry chloroform. 11 mmol of thionylchloride (0.81 mL) was added and the solution heated to 80° C. for 1 hour. A new portion of 0.8 mL of thionylchloride and more chloroform-dimethylformamide were then added and heating continued for 3 hours. The solvents were evaporated in vacuo and the rest partitioned between water-chloroform. The organic extract was dried and used in next reaction without purification. The chloroform solution was heated with excess of 2-hydroxybenzylamine and N-ethyldiisopropylamine for 1 hour. The product was purified by column chromatography (silica gel, chloroform-MeOH-AcOH (20:0.4:0.1)). M.p.205–210° C. Yield 40%. MS-ESI(+)m/z 297 [M+H]$^+$ Example 10

6-(Benzylamino)-2-[(1-hydroxymethyl)propylamino]-8-chloro-9-isopropylpurine. 6-(Benzylamino)-2,8-dichloropurine, prepared from 2,6,8-trichloropurine, m.p.220–223° C., 50% yield, was dissolved in 2-aminobutanol and heated to 150° C. for 12 hours. After evaporation of the solvent in vacuo the product, 6-benzylamino-2-[(1-hydroxymethyl)propylamino]-8-chloropurine was purified by column chromatography (silica gel, chloroform—MeOH—conc. NH$_4$OH 9:1:0.1) with total yield 36%. MS-ESI(+)m/z 348 [M+H]$^+$. The product was subsequently alkylated with isopropyliodide/K$_2$CO$_3$/dimethylformamide to give, after preparative column chromatography (silica gel, chloroform) 70% yield of the desired compound. MS (ESI+): 388.4,390.6 (M+H)$^+$.

Example 11

Preparation of Affinity Sorbent

Preparation of 2-(2-aminopropylamino)-6-(3-hydroxypropylamino)-8-bromo-9-isopropylpurine Epoxy activated Sepharose 6B Affinity Matrix Freeze-dried epoxy activated Sepharose 6B (Pharmacia LKB, Piscataway, N.J.) was chosen for the coupling reaction due to its ability to form an ether bond between a hydroxyl-containing ligand and the epoxide group on the Sepharose. The gel was swollen according to the manufacturer's instructions, (100 mg) of any one of the compound defined in claim 1 and 56 (preferably with R6=aminooctylamino, 3- or 4-benzylamino, etc.) was dissolved in 1 ml coupling solution (1.2:1, v/v, DMF, 0.1N NaOH) and mixed with 0.5 ml of swollen gel at pH 10–11 for 72 h at room temperature with gentle agitation. Excess reactive groups were blocked with 1M ethanolamine for 4 hours at 50° C. and the gel slurry was poured into 1-ml syringe column. The resin was activated with three alternating cycles of twenty column volumes each of pH 4.0 (0.1M acetate, 0.5 M NaCl) and pH 8.0 (0.1M tris-HCl, 0.5 M NaCl) buffers-followed by twenty column volumes of reaction buffer (20 mM HEPES, pH 7.3, 10 mM $MgCl_2$, 15 mM glycerophosphate, 0.5 mM sodium orthovanadate, 0.5 mM EGTA). The column was stored at 4° C. in the reaction buffer containing 0.1% sodium azide and regenerated prior to each use with alternating cycles of low and high pH as described above.

The Sf9 insect cell lysate (500 μg protein in 1-ml reaction buffer) was passed. over the affinity column matrix sequentially five times and the flow through was saved (unbound material). The matrix was then washed three times with 1 ml reaction buffer (wash 1–3) then three times each reaction buffer containing 0.5M NaCl (eluate 1–3). The coupled proteins were eluted at low pH (pH 4.0, 0.1M acetate, 0.5M NaCl) as described above and aliquots (20 μl from 1 ml) of each sample were assayed for their ability to phosphorylate histone H1 and other substrate proteins as described in Example 12. The presence of CDK complexes was also determined by SDS-PAGE.

Example 12

CDK Inhibition Assays

Proteins

Cyclin-dependent kinases ($p34^{cdc2}$, $p33^{cdk2}$, $p33^{cdk4}$) and cyclins (cyclin B, E and D1) are produced in Sf9 insect cells coinfected with appropriate baculoviral constructs. The cells are harvested 68–72 hrs post infection in lysis buffer for 30 min on ice and the soluble fraction is recovered by centrifugation at 14.000 g for 10 min. The protein extract is stored at −80° C.

Rb-GST is produced using an E. coli expression system, containing sequence encoding C terminus of retinoblastoma protein (aminoacids 773–928), which is known to be phosphorylated by $p33^{cdk4}$ kinase. The fusion protein is purified on glutathione-agarose beads.

Lysis buffer: 50 mM Tris pH 7,4, 150 mM NaCl, 5 mM EDTA, 20 mM NaF, 1% Tween, 1 mM DTT, 0.1 mM PMSF, leupeptine, aprotomine Enzyme Inhibition Assays To carry out experiments on kinetics under linear conditions, the final point test system for kinase activity measurement is used. The kinase is added to reaction mixture in such a way as to obtain linear activity with respect to the concentration of enzyme and with respect to time.

The $p34^{cdc2}$ and $p33^{cdk2}$ kinase inhibition determination involves the use of 1 mg/ml histone H1 (Sigma, type III-S) in the presence of 15 μM [γ-$^{32}$P]ATP (500–100 cpm/pmol) (Amersham) in a final volume of 20 μl, inhibition of $p33^{cdk4}$ kinase is determined with Rb-GST (0,2 mg/ml) as a substrate. Kinase activity is determined at 30° C. in the kinase buffer.

Tested compounds are usually dissolved to 100 mM solutions in DMSO, final concentration of DMSO in reaction mixture never exceeds 1%. The controls contain suitable dilutions of DMSO.

After 10 min, addition 3×SDS sample buffer stops the incubations. Phosphorylated proteins are separated electrophoretically using 12.5% SDS polyacrylamide gel. The measurement of kinase activity is done using digital image analysis.

The kinase activity is expressed as a percentage of maximum activity, the apparent inhibition constants are determined by graphic analysis. Kinase buffer: 50 mM Hepes pH 7.4, 10 mM $MgCl_2$, 5 mM EGTA, 10 mM 2-glycerolphosphate, 1 mM NaF, 1 mM DTT

TABLE 4

Kinase Inhibitory Activity of 2,6,8,9-Tetrasubstituted Purine Derivatives

| SUBSTITUENT | | | | CDC2 | IκB-α |
|---|---|---|---|---|---|
| C2 | N6 | C8 | N9 | $IC_{50}$ (μM) | $IC_{50}$ (μM) |
| 2-hydroxyethylamino OLOMOUCINE | benzylamino | — | methyl | 7 | 15.4 |
| 2-hydroxyethylamino | benzylamino | fluoro | methyl | 4.2 | 7.8 |
| 2-hydroxyethylamino | benzylamino | bromo | methyl | 16.2 | 22.8 |
| 2-hydroxyethylamino | benzylamino | mercapto | methyl | 22.4 | 35.7 |
| 2-hydroxyethylamino | benzylamino | hydroxy | methyl | 13.5 | 16.2 |
| 2-hydroxyethylamino | benzylamino | amino | methyl | 14.2 | 17.1 |
| 2-hydroxyethylamino | benzylamino | 2-hydroxyethylamino | methyl | 125.2 | 153.8 |
| 2-hydroxyethylamino | benzylamino | aminomethylamino | methyl | 114.3 | 126.5 |
| 3-hydroxypropylamino | benzylamino | — | isopropyl | 1 | 3.2 |

TABLE 4-continued

Kinase Inhibitory Activity of 2,6,8,9-Tetrasubstituted Purine Derivatives

| SUBSTITUENT | | | | CDC2 | IκB-α |
|---|---|---|---|---|---|
| C2 | N6 | C8 | N9 | IC$_{50}$ (μM) | IC$_{50}$ (μM) |
| BOHEMINE | | | | | |
| 3-hydroxypropylamino | benzylamino | bromo | isopropyl | 12.93 | 24.5 |
| 3-hydroxypropylamino | benzylamino | mercapto | isopropyl | 13.1 | 20.9 |
| 3-hydroxypropylamino | benzylamino | hydroxy | isopropyl | 6.48 | 12.6 |
| 3-hydroxypropylamino | benzylamino | amino | isopropyl | 8.52 | 12.8 |
| 3-hydroxypropylamino | benzylamino | 2-hydroxyethylamino | isopropyl | 143.8 | 152.6 |
| 3-hydroxypropylamino | benzylamino | aminomethylamino | isopropyl | 123.5 | 138.7 |
| (R)-1-(hydroxymethyl)propylamino | benzylamino | | isopropyl | 0.45 | 1.4 |
| ROSCOVITINE | | | | | |
| (R)-1-(hydroxymethyl)propylamino | benzylamino | fluoro | isopropyl | 0.38 | 1.2 |
| (R)-1-(hydroxymethyl)propylamino | benzylamino | bromo | isopropyl | 10.38 | 11.2 |
| (R)-1-(hydroxymethyl)propylamino | benzylamino | mercapto | isopropyl | 41.11 | 43.8 |
| (R)-1-(hydroxymethyl)propylamino | benzylamino | hydroxy | isopropyl | 10.15 | 10.94 |
| (R)-1-(hydroxymethyl)propylamino | benzylamino | amino | isopropyl | 20.17 | 20.85 |
| (R)-1-(hydroxymethyl)propylamino | benzylamino | 2-hydroxyethylamino | isopropyl | 151.93 | 164.95 |
| (R)-1-(hydroxymethyl)propylamino | benzylamino | aminomethylamino | isopropyl | 181.05 | 193.28 |
| (R)-1-(hydroxymethyl)isobutylamino | 3-chloroanilino | | isopropyl | 4 nM | 11.2 nM |
| PURVALANOL A | | | | | |
| (R)-1-(hydroxymethyl)isobutylamino | 3-chloroanilino | fluoro | isopropyl | 3.8 nM | 11 nM |
| (R)-1-(hydroxymethyl)isobutylamino | 3-chloroanilino | bromo | isopropyl | 43.8 nM | 51 nM |
| (R)-1-(hydroxymethyl)isobutylamino | 3-chloroanilino | mercapto | isopropyl | 83.7 nM | 105.6 nM |
| (R)-1-(hydroxymethyl)isobutylamino | 3-chloroanilino | hydroxy | isopropyl | 72.1 nM | 89.5 nM |
| (R)-1-(hydroxymethyl)isobutylamino | 3-chloroanilino | amino | isopropyl | 91.5 nM | 92.8 nM |
| (R)-1-(hydroxymethyl)isobutylamino | 3-chloroanilino | 2-hydroxyethylamino | isopropyl | 1529.6 nM | 1726.8 nM |
| (R)-1-(hydroxymethyl)isobutylamino | 3-chloroanilino | aminomethylamino | isopropyl | 2521.3 nM | 3287.2 nM |

Table 4 shows the results of inhibitory activity of novel compounds against CDC2 and IκB-α in comparison with the data on the prototype compounds. Most of the 2,6,8,9-tetrasubstituted purine derivatives showed marked inhibitory activity in in vitro kinase assays. Modification of 2,6,8-trisubstituted purines by small substituent in R8 position led usually to increase in cdk inhibitory acitvity of the tested compound.

Example 13

Antimitotic Activities of CDK Inhibitors

Metaphase-arrested Xenopus egg extracts were prepared as described previously by Blow "J.Cell Biol." 122:993 (1993) and stored in liquid nitrogen. Demembranated Xenopus sperm nuclei were prepared as described by Blow & Laskey "Cell" 47:577 (1986). After thawing, extracts were supplemented with 25 mM phosphocreatine, 5 μg/ml creatine phosphokinase, 250 μg/ml cycloheximide, [α-$^{32}$P]dATP (for DNA synthesis assays). Demembranated sperm nuclei were added to a final sperm concentration of 3 g/μl DNA extract and CDK inhibitor tested was then added at different concentrations. M-phase promoting factor inhibition by different CDK inhibitors was monitored 1.5 h after addition by assessing the amount of sperm nuclei that had been assembled into interphase nuclei, possessing a complete phase-dense nuclear envelope. DNA synthesis was assessed by releasing extract into interphase by the addition of 0.3 mM CaCl$_2$ and measuring the total amount of [α-$^{32}$P]dATP incorporation after 3 h by TCA co-precipitation.

At concentrations of CDK inhibitors (see Table 5) ranging from 0.1–2 μM, chromosomes remained highly condensed and no nuclear envelope was visible. At 4–6 μM and higher concentrations, interphase nuclei appeared with partially decondensed chromatin and an intact nuclear envelope. Replication was significantly inhibited at 1–5 μM CDK inhibitors tested. For the inhibition effect to become detectable, the first 15-min incubation of the interphase extract is probably sufficient.

TABLE 5

Antimitotic Activities of 2,6,8,9-Tetrasubstituted Purine Derivatives

| SUBSTITUENT | | | | Inhibition of MPF activity | Inhibition of DNA synthesis |
|---|---|---|---|---|---|
| C2 | N6 | C8 | N9 | IC$_{50}$ (μM) | IC$_{50}$ (μM) |
| hydroxyethylamino | benzylamino | — | methyl | 12 | 15 |
| OLOMOUCINE | | | | | |
| hydroxypropylamino | benzylamino | fluoro | isopropyl | 2.6 | 3.2 |
| (R)-1-(hydroxymethyl)propylamino | benzylamino | fluoro | isopropyl | 1.5 | 2.4 |
| (R)-1-(hydroxymethyl)propylamino | 3-chloroanilino | fluoro | isopropyl | 0.8 | 1.5 |

TABLE 5-continued

Antimitotic Activities of 2,6,8,9-Tetrasubstituted Purine Derivatives

| SUBSTITUENT | | | | Inhibition of MPF activity | Inhibition of DNA synthesis |
|---|---|---|---|---|---|
| C2 | N6 | C8 | N9 | $IC_{50}$ ($\mu$M) | $IC_{50}$ ($\mu$M) |
| (R)-1-(hydroxymethyl)propylamino | 3-chloro-4-carboxyanilino | fluoro | isopropyl | 0.1 | 0.25 |
| (R)-1-(hydroxymethyl)propylamino | 3-chloroanilino | amino | isopropyl | 3.12 | 3.3 |
| (R)-1-(hydroxymethyl)propylamino | 3-chloroanilino | hydroxy | isopropyl | 4.08 | 4.2 |
| 2-hydroxyethylamino | 3-chloroanilino | 3-hydroxyethylamino | isopropyl | 41.7 | 63.5 |
| (R)-1-(hydroxymethyl)propylamino | 3-chloroanilino | bromo | isopropyl | 31.6 | 52.8 |

Example 14

In vitro Cytotoxic Activity of Novel Compounds

One of the parameters used, as the basis for colorimetric assays, is the metabolic activity of viable cells. For example, a microtiter assay, which uses the tetrazolium salt MTT, is now widely used to quantitate cell proliferation and cytotoxicity. For instance, this assay is used in drug screening programs and in chemosensitivity testing. Because only metabolically active cells cleave tetrazolium salts, these assays detect viable cells exclusively. In the case of MTT assay, yellow soluble tetrazolium salt is reduced to coloured water-insoluble formazan salt. After it is solubilized, the formazan formed can easily and rapidly be quantified in a conventional ELISA plate reader at 570 nm (maximum absorbance). The quantity of reduced formazan corresponds to number of vital cells in the culture.

Human T-lymphoblastic leukemia cell line CEM; promyelocytic HL-60 and monocytic U937 leukemias; breast carcinoma cell lines MCF-7, BT549, MDA-MB-231; glioblastoma U87MG cells; cervical carcinoma cells HELA; sarcoma cells U2OS and Saos2; hepatocellular carcinoma HepG2; mouse fibroblasts NIH3T3; mouse immortalized bone marrow macrophages B2.4 and B10A.4; P388D1 and L1210 leukemia; B16 and B16F10 melanomas were used for routine screening of compounds. The cells were maintained in Nunc/Corning 80 cm² plastic tissue culture flasks and cultured in cell culture medium (DMEM with 5 g/l glucose, 2 mM glutamine, 100 U/ml penicillin, 100 $\mu$g/ml streptomycin, 10% fetal calf serum and sodium bicarbonate).

The cell suspensions that were prepared and diluted according to the particular cell type and the expected target cell density (2.500–30.000 cells per well based on cell growth characteristics) were added by pipette (80 $\mu$l) into 96/well microtiter plates. Inoculates were allowed a pre-incubation period of 24 hours at 37° C. and 5% $CO_2$ for stabilisation. Four-fold dilutions of the intended test concentration were added at time zero in 20 $\mu$l aliquots to the microtiter plate wells. Usually, test compound was evaluated at six 4-fold dilutions. In routine testing, the highest well concentration was 266.7 $\mu$M, but it can be the matter of change dependent on the agent. All drug concentrations were examined in duplicates. Incubations of cells with the test compounds lasted for 72 hours at 37° C., in 5% $CO_2$ atmosphere and 100% humidity. At the end of incubation period, the cells were assayed by using the MTT. Ten microliters of the MTT stock solution were pipetted into each well and incubated further for 1–4 hours. After this incubation period, formazan was solubilized by addition of 100 $\mu$l/well of 10% SDS in water (pH=5.5) followed by further incubation at 37° C. overnight. The optical density (OD) was measured at 540 nm with the Labsystem iEMS Reader MF (UK). The tumour cell survival (TCS) was calculated using the following equitation: TCS=($OD_{drug\ exposed\ well}$/mean $OD_{control\ wells}$)×100%. The $TCS_{50}$ value, the drug concentration lethal to 50% of the tumour cells, was calculated from the obtained dose response curves.

Cytoxicity of novel compounds was tested on panel of cell lines of different histogenetic and species origin (Table 6). We show here that equal activities were found in all tumour cell lines tested, however, the non-malignant cells, e.g. NIH3T3 fibroblasts and normal hums lymphocytes, were resistant to synthetic CDK inhibitors induced cytotoxicity. As demonstrated in Table 6, $IC_{50}$ for NIH3T3 fibroblasts and normal human lymphocytes was always higher than 250 $\mu$M. Effective novel derivatives killed tumour cells in concentrations close to 1–5 $\mu$M. Notably, the identical effectiveness of purine derivatives was also found in cell lines bearing various mutations or deletions in cell cycle associated proteins, e.g. HL-60, BT549, Hela, U2OS, MDA-MB231, and Saos2 (Table 6). It indicates that these substances should be equally effective in tumours with various alterations of tumour suppresser genes, namely p53, Rb, etc. Importantly, this observation distinguishes novel compounds from flavopiridol and related compounds, as their biological activity is dependent on p53 status.

TABLE 6

Cytotoxicity of Novel Compounds for Different Cancer Cells

| SUBSTITUENT | | | | CEM | B16 |
|---|---|---|---|---|---|
| C2 | N6 | C8 | N9 | $IC_{50}$ ($\mu$M) | $IC_{50}$ ($\mu$M) |
| 2-hydroxyethylamino OLOMOUCINE | benzylamino | — | methyl | 70 | 85.4 |
| 2-hydroxyethylamino | benzylamino | fluoro | methyl | 45.2 | 62.8 |
| 2-hydroxyethylamino | benzylamino | bromo | methyl | 165.2 | 172.8 |

TABLE 6-continued

Cytotoxicity of Novel Compounds for Different Cancer Cells

| SUBSTITUENT | | | | CEM | B16 |
|---|---|---|---|---|---|
| C2 | N6 | C8 | N9 | IC$_{50}$ ($\mu$M) | IC$_{50}$ ($\mu$M) |
| 2-hydroxyethylamino | benzylamino | mercapto | methyl | 92.4 | 85.7 |
| 2-hydroxyethylamino | benzylamino | hydroxy | methyl | 45.5 | 56.2 |
| 2-hydroxyethylamino | benzylamino | amino | methyl | 84.2 | 67.1 |
| 2-hydroxyethylamino | benzylamino | 2-hydroxyethylamino | methyl | >166.7 | >166.7 |
| 2-hydroxyethylamino | benzylamino | aminomethylamino | methyl | 14.3 | 126.5 |
| 3-hydroxypropylamino | benzylamino | — | isopropyl | 4.1 | 7.2 |
| BOHEMINE | | | | | |
| 3-hydroxypropylamino | benzylamino | fluoro | isopropyl | 3.93 | 5.5 |
| 3-hydroxypropylamino | benzylamino | bromo | isopropyl | 116.9 | 76.4 |
| 3-hydroxypropylamino | benzylamino | methylthio | isopropyl | 68.4 | 60.6 |
| 3-hydroxypropylamino | benzylamino | hydroxy | isopropyl | 7.48 | 5.6 |
| 3-hydroxypropylamino | benzylamino | amino | isopropyl | 8.52 | 6.8 |
| 3-hydroxypropylamino | benzylamino | 2-hydroxyethylamino | isopropyl | >166.7 | >166.7 |
| 3-hydroxypropylamino | benzylamino | 2-aminoethylamino | isopropyl | 29.9 | 2.5 |
| (R)-1-(hydroxymethyl)propylamino | benzylamino | | isopropyl | 3.45 | 4.4 |
| ROSCOVITINE | | | | | |
| (R)-1-(hydroxymethyl)propylamino | benzylamino | fluoro | isopropyl | 3.38 | 3.2 |
| (R)-1-(hydroxymethyl)propylamino | benzylamino | bromo | isopropyl | 48.4 | 59.2 |
| (R)-1-(hydroxymethyl)propylamino | benzylamino | mercapto | isopropyl | 30.7 | 125.6 |
| (R)-1-(hydroxymethyl)propylamino | benzylamino | hydroxy | isopropyl | 12.15 | 12.94 |
| (R)-1-(hydroxymethyl)propylamino | benzylamino | amino | isopropyl | 12.17 | 12.85 |
| (R)-1-(hydroxymethyl)propylamino | benzylamino | 2-hydroxyethylethoxy | isopropyl | 140.2 | 124.95 |
| (R)-1-(hydroxymethyl)propylamino | benzylamino | 1,2-dihydroxypropylamino | isopropyl | 128.2 | 147.5 |
| (R)-1-(hydroxymethyl)propylamino | benzylamino | 2-aminoethylamino | isopropyl | 96.1 | >166.7 |
| (R)-1-(hydroxymethyl)propylamino | benzylamino | hydrazido | isopropyl | 58 | 61.5 |
| (R)-1-(hydroxymethyl)isobutylamino | 3-chloroanilino | | isopropyl | 2.4 | 3.5 |
| PURVALANOL A | | | | | |
| (R)-1-(hydroxymethyl)isobutylamino | 3-chloroanilino | fluoro | isopropyl | 2.5 | 3.5 |
| (R)-1-(hydroxymethyl)isobutylamino | 3-chloroanilino | bromo | isopropyl | 22.5 | 23.5 |
| (R)-1-(hydroxymethyl)isobutylamino | 3-chloroanilino | mercapto | isopropyl | 25.8 | 47.6 |
| (R)-1-(hydroxymethyl)isobutylamino | 3-chloroanilino | hydroxy | isopropyl | 11.8 | 11.3 |
| (R)-1-(hydroxymethyl)isobutylamino | 3-chloroanilino | amino | isopropyl | 11.5 | 11.8 |
| (R)-1-(hydroxymethyl)isobutylamino | 3-chloroanilino | 2-hydroxyethylamino | isopropyl | 78 | 150 |
| (R)-1-(hydroxymethyl)isobutylamino | 3-chloroanilino | 2-aminomethylamino | isopropyl | 56 | 130 |

Example 15

Novel Compounds Induce Apoptosis in Tumour Cells

To analyse the mechanisms of induced cytotoxicity by novel compounds, it is important to distinguish apoptosis from the other major form of cell death, necrosis. First, at the tissue level, apoptosis produces little or no inflammation, since the neighbouring cells, especially macrophages, rather than being released into the extracellular fluid, engulf shrunken portions of the cell. In contract, in necrosis, cellular contents are released into the extracellular fluid, and thus have an irritant affect on the nearby cells, causing inflammation. Second, at the cellular level, apoptotic cells exhibit shrinkage and blebbing of the cytoplasm, preservation of structure of cellular organelles including the mitochondria, condensation and margination of chromatin, fragmentation of nuclei, and formation of apoptotic bodies, thought not all of these are seen in all cell types. Third, at the molecular level, a number of biochemical processes take an important role in induction of apoptosis. However, majority of them is not well understood, and they result in activation of proteases and nucleases, which finally destruct key biological macromolecules—proteins and DNA. For detection of apoptotic versus necrotic mode of cell death, two independent methods were employed: assessment of morphology by electron microscopy and analysis of DNA fragmentation by flow-cytometry.

HL-60 cell line was cultured in 6-well culture plates with or without 70 $\mu$M concentration of novel derivatives at 37° C. and 5% CO$_2$ for 3–24 hours. Following the incubation, cells were pelleted, washed in Hank's buffered salt solution and processed as described below.

Cells were suspended in 2% glutaraldehyde/PBS, fixed overnight at 4° C., pelleted and embedded into 1% agar (Agar Noble, Difco) thereafter. Agar block containing fixed cells was epoxide polymerised, ultrathin sectioned, osmium tetraoxide postfixed, uranium acetate contrasted and examined under electron microscope.

Initial phase contrast microscopy examinations indicated that treated HL-60 line exhibit typical morphological features of apoptotic cells, and it was later confirmed by electron microscopy. Typical morphological criteria of apoptosis were identified in cells treated with tetrasubstituted purine derivatives: chromatin condensation, nuclear fragmentation, cytoplasmatic blebbing, and formation of apoptotic bodies.

Example 16

Immunosuppressive Activity

One of the most important parameters of specific cellular immunity is proliferative response of lymphocytes to antigens or polyclonal mitogens. Majority of normal mammalian peripheral lymphocytes is resting cells. Antigens or nonspecific—polyclonal mitogens have capacity to activate lymphoid cells and it is accompanied with dramatic changes of intracellular metabolism (mitochondrial activity, protein synthesis, nucleic acids synthesis, formation of blastic cells and cellular proliferation). Compounds with ability to selectively inhibit lymphocyte proliferation are potent immunosuppressants. Variety of in vitro assays were developed to measure proliferative response of lymphocytes. The most commonly used is $^3$H-thymidine incorporation method.

During cell proliferation, the DNA has to be replicated before the cell is divided into two daughter cells. This close association between cell doublings and DNA synthesis is very attractive for assessing cell proliferation. If labeled DNA precursors are added to the cell culture, cells that are about to divide incorporate the labeled nucleotide into their DNA. Traditionally, those assays usually involve the use of radiolabeled nucleosides, particularly tritiated thymidine ([$^3$H]-TdR). The amount of [$^3$H]-TdR incorporated into the cellular DNA is quantified by liquid scintillation counting.

Human heparinized peripheral blood was obtained from healthy volunteers by cubital vein punction. The blood was diluted in PBS (1:3) and mononuclear cells were separated by centrifugation in Ficoll-Hypaque density gradient (Pharmacia, 1.077 g/ml) at 2200 g for 30 minutes. Following centrifugation, lymphocytes were washed in PBS and resuspended in cell culture medium (RMPI 1640, 2 mM glutamine, 100 U/ml penicillin, 100 µg/ml streptomycin, 10% fetal calf serum and sodium bicarbonate).

The cells were diluted at target density of 1.100.000 cells/ml were added by pipet (180 µl) into 96/well microtiter plates. Four-fold dilutions of the intended test concentration were added at time zero in 20 µl aliquots to the microtiter plate wells. Usually, test compound was evaluated at six 4-fold dilutions. In routine testing, the highest well concentration was 266.7 µM. All drug concentrations were examined in duplicates. All wells with exception of unstimulated controls were activated with 50 µl of concanavalin A (25 µg/ml). Incubations of cells with test compounds lasted for 72 hours at 37° C., in 5% $CO_2$ atmosphere and 100% humidity. At the end of incubation period, the cells were assayed by using the [$^3$H]-TdR:

Cell cultures were incubated with 0.5 µCi (20 µl of stock solution 500 µCi/ml) per well for 6 hours at 37° C. and 5% $CO_2$. The automated cell harvester was used to lyse cells in water and adsorb the DNA onto glass-fiber filters in the format of microtiter plate. The DNA incorporated [$^3$H]-TdR was retained on the filter while unincorporated material passes through. The filters were dried at room temperature overnight, sealed into a sample bag with 10–12 ml of scintillant. The amount of [$^3$H]-TdR present in each filter (in CCPM) was determined by scintillation counting in a Beta-plate liquid scintillation counter. The effective dose of immunosuppressant (ED) was calculated using the following equotation: ED=($CCPM_{drug\ exposed\ well}$/mean $CCPM_{control\ wells}$)×100%. The $ED_{50}$ value, the drug concentration inhibiting proliferation of 50% of lymphocytes, was calculated from the obtained dose response curves.

To evaluate immunosuppressive activity of tetrasubstituted adenines, their ability to inhibit polyclonal mitogen induced proliferation of normal human lymphocytes was analyzed (Table 7). Our data demonstrate that these compounds have only marginal activity on $^3$H-thymidine incorporation, nonetheless, they efficiently inhibit proliferation of activated lymphocytes. Effective immunosuppressive dose of tetrasubstituted derivatives under in vitro conditions was close to 1–20 µM.

TABLE 7

Immunosuppressive effects of compounds on spontaneous and mitogen activated proliferation of lymphocytes

| SUBSTITUENT | | | | spontaneous | mitogen activated |
|---|---|---|---|---|---|
| C2 | N6 | C8 | N9 | $IC_{50}$ (µM) | $IC_{50}$ (µM) |
| hydroxyethylamino<br>OLOMOUCIN | benzylamino | — | methyl | 245 | 72.1 |
| 2-hydroxyethylamino | benzylamino | bromo | methyl | 228 | 68.3 |
| 2-hydroxyethylamino | benzylamino | mercapto | methyl | 250 | 83.5 |
| 2-hydroxyethylamino | benzylamino | hydroxy | methyl | 201 | 48.6 |
| 2-hydroxyethylamino | benzylamino | amino | methyl | 170.3 | 26.7 |
| 2-hydroxyethylamino | benzylamino | 2-hydroxyethylamino | methyl | 250 | 169.3 |
| 2-hydroxyethylamino | benzylamino | aminomethylamino | methyl | 250 | 113.5 |
| 3-hydroxypropylamino<br>BOHEMIN | benzylamino | — | isopropyl | 172 | 5.7 |
| 3-hydroxypropylamino | benzylamino | bromo | isopropyl | 178 | 5.9 |
| 3-hydroxypropylamino | benzylamino | mercapto | isopropyl | 197 | 18.4 |
| 3-hydroxypropylamino | benzylamino | hydroxy | isopropyl | 163 | 2.1 |
| 3-hydroxypropylamino | benzylamino | amino | isopropyl | 143 | 1.59 |
| 3-hydroxypropylamino | benzylamino | 2-hydroxyethylamino | isopropyl | 181 | 29.3 |
| 3-hydroxypropylamino | benzylamino | aminomethylamino | isopropyl | 174 | 26.8 |
| (R)-1-(hydroxymethyl)propylamino<br>ROSCOVITIN | benzylamino | | isopropyl | 164 | 6.4 |
| (R)-1-(hydroxymethyl)propylamino | benzylamino | bromo | isopropyl | 168 | 17.1 |
| (R)-1-(hydroxymethyl)propylamino | benzylamino | mercapto | isopropyl | 174 | 18.5 |
| (R)-1-(hydroxymethyl)propylamino | benzylamino | hydroxy | isopropyl | 153 | 12.8 |
| (R)-1-(hydroxymethyl)propylamino | benzylamino | amino | isopropyl | 149 | 13.3 |
| (R)-1-(hydroxymethyl)propylamino | benzylamino | 2-hydroxyethylamino | isopropyl | 182 | 31.5 |
| (R)-1-(hydroxymethyl)propylamino | benzylamino | aminomethylamino | isopropyl | 177 | 25.8 |
| (R)-1-(hydroxymethyl)isobutylamino | 3-chloroanilino | | isopropyl | 158 | 5.7 |

TABLE 7-continued

Immunosuppressive effects of compounds on spontaneous and mitogen activated proliferation of lymphocytes

| SUBSTITUENT | | | | spontaneous | mitogen activated |
|---|---|---|---|---|---|
| C2 | N6 | C8 | N9 | IC$_{50}$ ($\mu$M) | IC$_{50}$ ($\mu$M) |
| PURVALANOL A | | | | | |
| (R)-1-(hydroxymethyl)isobutylamino | 3-chloroanilino | bromo | isopropyl | 142 | 13.7 |
| (R)-1-(hydroxymethyl)isobutylamino | 3-chloroanilino | mercapto | isopropyl | 164 | 26.9 |
| (R)-1-(hydroxymethyl)isobutylamino | 3-chloroanilino | hydroxy | isopropyl | 126 | 2.98 |
| (R)-1-(hydroxymethyl)isobutylamino | 3-chloroanilino | amino | isopropyl | 103 | 3.1 |
| (R)-1-(hydroxymethyl)isobutylamino | 3-chloroanilino | 2-hydroxyethylamino | isopropyl | 205 | 150 |
| (R)-1-(hydroxymethyl)isobutylamino | 3-chloroanilino | aminomethylamino | isopropyl | 230 | 138 |

Example 17

Antiviral Activity

The activity of the compounds against HIV-1 and HIV-2 induced cytopahicity was examined in human lymphocyte MT-4 cells. The cells (300 000 cells/ml) were infected with 100 CCID$_{50}$ (1 CCID$_{50}$ is a virus quantity which causes cytopathicity effect in 50% of the cells under the experimental conditions) of HIV-1 or HIV-2 and added to 200 $\mu$l wells of a microtiter plate containing different dilutions of the tested compounds. The infected cell cultures were incubated at 37° C. for 5 days in a humidified CO$_2$ incubator. The cytopathicity of the virus was examined by determination of MT-4 cell viability by trypan blue dye staining. The results are summarised in Table 8 with comparison on the prototype compounds.

Table 8 also shows the results of activity testing of novel compounds against MSV-induced transformation in murine embryo fibroblast C3H/3T3 cells. The cells were seeded in 1 ml wells of 48-well plates and exposed to 80 PFU (plague forming units) for 60–90 min. The virus was subsequently removed and culture medium containing appropriate concentrations of the tested compounds was added (1 ml per well). At day 6-post infection, MSV-induced transformation of the cell culture was examined microscopically.

TABLE 8

Antiretroviral Activity of Purine Compounds, wherein R9 is either PMP-(2-phosphonomethoxypropyl)group or PME(2-phosphonomethoxyethyl)-group. ($\mu$g/ml), (R2 = NH$_2$).

| | | | HIV-1 | | HIV-2 | |
|---|---|---|---|---|---|---|
| R6 | R8 | MSV | MT-4 | CEM | MT-4 | CEM |
| PME-derivatives | | | | | | |
| amino | | 0.6 | 2.67 | 6.9 | ND | ND |
| amino | fluoro | 0.57 | 3.12 | 7.2 | ND | ND |
| amino | mercapto | 1.23 | 5.87 | 10.8 | ND | ND |
| amino | hydroxy | 0.42 | 1.95 | 5.2 | ND | ND |
| amino | amino | 0.58 | 1.98 | 4.8 | ND | ND |
| amino | 2-hydroxy-ethylamino | 1.54 | 8.33 | 10.8 | ND | ND |
| amino | aminomethyl-amino | 1.32 | 7.54 | 9.3 | ND | ND |
| cyclohexyl-amino | | 0.26 | 5.7 | >20 | 4.8 | >20 |
| cyclohexyl-amino | fluoro | 0.24 | 6.3 | >20 | 4.6 | >20 |
| cyclohexyl-amino | mercapto | 0.35 | 8.9 | >20 | 8.5 | >20 |
| cyclohexyl-amino | hydroxy | 0.21 | 4.3 | >20 | 2.1 | >20 |
| cyclohexyl-amino | amino | 0.19 | 3.5 | >20 | 1.6 | >20 |
| cyclohexyl-amino | 2-hydroxy-ethylamino | 0.45 | 12.7 | >20 | 12.7 | >20 |
| cyclohexyl-amino | aminomethyl-amino | 0.43 | 10.8 | >20 | 9.5 | >20 |
| benzylamino | | 1.5 | 50 | >20 | 49 | >20 |
| benzylamino | fluoro | 1.3 | 47 | >20 | 45 | >20 |
| benzylamino | mercapto | 1.8 | 56 | >20 | 57 | >20 |
| benzylamino | hydroxy | 0.9 | 45 | >20 | 32 | >20 |
| benzylamino | amino | 0.8 | 48 | >20 | 31 | >20 |
| benzylamino | 2-hydroxy-ethylamino | 1.7 | 67 | >20 | 48 | >20 |
| benzylamino | aminomethyl-amino | 1.4 | 55 | >20 | 52 | >20 |
| PMP-derivatives | | | | | | |
| amino | | 0.07 | 0.29 | 10 | 0.24 | 10 |
| amino | fluoro | 0.06 | 3.12 | ND | 3.54 | ND |
| amino | mercapto | 0.15 | 4.18 | ND | 4.15 | ND |
| amino | hydroxy | 0.05 | 0.25 | ND | 0.21 | ND |
| amino | amino | 0.06 | 0.19 | ND | 0.20 | ND |
| amino | 2-hydroxy-ethylamino | 0.35 | 5.16 | ND | 4.87 | ND |
| amino | aminomethyl-amino | 0.42 | 4.58 | ND | 4.65 | ND |
| cyclohexyl-amino | | 3.78 | 3.4 | 4.5 | 5.8 | 8.5 |
| cyclohexyl-amino | fluoro | 2.54 | 3.2 | 4.1 | 4.6 | 8.3 |
| cyclohexyl-amino | mercapto | 6.32 | 10.1 | >20 | 11.2 | >20 |
| cyclohexyl-amino | hydroxy | 1.37 | 2.1 | 5.2 | 3.2 | 7.8 |
| cyclohexyl-amino | amino | 1.25 | 1.8 | 4.7 | 2.8 | 8.1 |
| cyclohexyl-amino | 2-hydroxy-ethylamino | 5.42 | 12.7 | >20 | 25.1 | >20 |
| cyclohexyl-amino | aminomethyl-amino | 4.98 | 9.8 | >20 | 18.6 | >20 |
| benzylamino | | 0.3 | 10.3 | 11.6 | 8.3 | 12.5 |
| benzylamino | fluoro | 0.27 | 8.5 | 12.5 | 6.4 | 11.1 |
| benzylamino | mercapto | 1.35 | 21.8 | >20 | >20 | >20 |
| benzylamino | hydroxy | 0.21 | 3.7 | 10.3 | 4.3 | 11.1 |
| benzylamino | amino | 0.18 | 2.9 | 10.7 | 3.8 | 11.9 |
| benzylamino | 2-hydroxy-ethylamino | 2.17 | 19.5 | >20 | >20 | >20 |

TABLE 8-continued

Antiretroviral Activity of Purine Compounds, wherein R9 is either PMP-(2-phosphonomethoxypropyl)group or PME(2-phosphonomethoxyethyl)-group. (μg/ml), (R2 = NH₂).

| R6 | R8 | MSV | HIV-1 MT-4 | CEM | HIV-2 MT-4 | CEM |
|---|---|---|---|---|---|---|
| benzylamino | aminomethyl-amino | 1.89 | 16.8 | >20 | >20 | >20 |

Most of the PMP (9-(2-phosphonomethoxypropyl) derivative) and PME (9-(2-phosphonomethoxyethyl) derivative) compounds of the formula I showed marked anti-HIV activity in vitro. HIV-1 and HIV-2 did not differ in their sensitivity to the test compounds. (R)-PMP compounds were markedly inhibitory to retroviruses at 2–3 μg/ml and not toxic to the cells at 100 μg/ml. Its selectivity index (ratio cytotoxic dose/antivirally active dose) proved superior over that of the prototype compound PME. The (S)-enantiomer of PME was devoid of marked antiretroviral activity. (R)-PMPD were exquisitely inhibitory to retrovirus replication (EC50 0.01–0.1 μg/ml) and not toxic to the cells at 100 μg/ml. It proved superior over PMEA and other prototype compounds in terms of both antiviral activity and lack of toxicity. Its selectivity index was higher than 2000 for HIV-1 and HIV-2.

Example 18

Dry Capsules 5000 capsules, each of which contain 0.25 g of one of the compounds of the formula I mentioned in the preceding Examples as active ingredient, are prepared as follows:

| Composition | |
|---|---|
| Active ingredient | 1250 g |
| Talc | 180 g |
| Wheat starch | 120 g |
| Magnesium stearate | 80 g |
| Lactose | 20 g |

Preparation process: The powdered substances mentioned are pressed through a sieve of mesh width 0.6 mm. Portions of 0.33 g of the mixture are transferred to gelatine capsules is with the aid of a capsule-filling machine.

Example 19

Soft Capsules 5000 soft gelatine capsules, each of which contain 0.05 g of one of the compounds of the formula I mentioned in the preceding Examples as active ingredient, are prepared as follows:

| Composition | |
|---|---|
| Active ingredient | 250 g |
| Lauroglykol | 2 liters |

Preparation process: The powdered active ingredient is suspended in Lauroglykol® (propylene glycol laurate, Gattefossé S. A., Saint Priest, France) and ground in a wet-pulveriser to a particle size of about 1 to 3 μm. Portions of in each case 0.419 g of the mixture are then transferred to soft gelatine capsules by means of a capsule-filling machine.

Example 20

Soft Capsules 5000 soft gelatine capsules, each of which contain 0.05 g of one of the compounds of the formula I mentioned in the preceding or following Examples as active ingredient, are prepared as follows:

| Composition | |
|---|---|
| Active ingredient | 250 g |
| PEG 400 | 1 liter |
| Tween 80 | 1 liter |

Preparation process: The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., USA, supplied by Sigma, Fluka, Aldrich) and ground in a wet-pulveriser to a particle size of about 1 to 3 mm. Portions of in each case 0.43 g of the mixture are then transferred to soft gelatine capsules by means of a capsule-filling machine.

What is claimed is:

1. Substituted nitrogen heterocyclic derivatives of the formula I

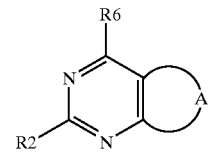

(I)

wherein

A is a divalent group selected from the ensemble consisting of

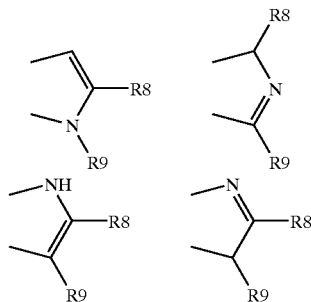

Z is N;

R2 and R6 are independent of one another, and represent
  H, halogen, alkyl, substituted alkyl, cycloalkyl, substituted cycloalkyl, cycloalkyl alkyl, arylalkyl, heteroalkyl, heteroarylalkyl, heterocycloalkyl alkyl or R6'—X, wherein
  X is an —NH—, —N(C₁—C₆-alkyl)—, —O— or —S— moiety;
  R6' is H, alkyl, substituted alkyl, acyl, amido, sulpho, cycloalkyl, substituted cycloalkyl, aryl, substituted aryl, heterocycle, heteroaryl, substituted heteroaryl, arylalkyl, heterocycloalkyl, substituted heterocycloalkyl, heteroarylalkyl, heteroalkyl, cycloalkyl alkyl and heterocycloalkyl alkyl; and R8 is hydroxyl, carboxyl, cyano, nitro, amido, sulpho, sulphamino, carbamino, cycloalkyl, substituted cycloalkyl, arylalkyl, heteroalkyl, heteroarylalkyl, cycloalkyl alkyl, heterocycloalkyl alkyl or R8'—X, wherein X is —N(alkyl)- or —S— moiety and R8' is according to any one of the substituents defined above for R2 or R6'; and R9 is alkyl, substituted alkyl, acyl, carboxyl, amido, sulphamino, cycloalkyl, substituted cycloalkyl, cycloalkyl alkyl, heteroalkylcycloalkyl alkyl, heterocycloalkyl, substituted heterocycloalkyl, aryl, arylalkyl, substituted aryl, heterocycle, heteroaryl, heteroarylalkyl, substituted heteroaryl, or —B—R9' wherein B is —CH$_2$—, —(CH$_2$)$_2$—, —CH(CH$_3$)CH$_2$—, —CH(CH$_2$F)CH$_2$—, —CH(CH$_2$OH)CH$_2$—, or the groups of the following structure,

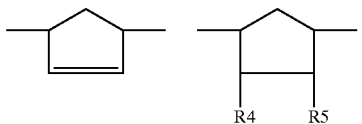

and

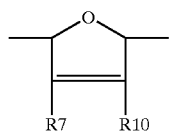

wherein the left hand bond is linked

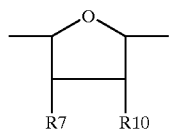

to nitrogen of 5-membered ring of compounds of the formula I; and wherein R4 and R5, that are independent of one another, represent hydrogen, hydroxyl, halogen, amino, acyloxy substituents having 1–5 carbon atoms, alkoxy substituents having 1–5 carbon atoms, alkylmercapto substituents having 1–5 carbon atoms, alkylamino substituents having 1–5 carbon atoms and dialkylamino in which each alkyl substituent has 1–5 carbon atoms;

R7 and R10, that are independent of one another, represent H or alkyl substituent having 1–10 carbon atoms;

or R9 is —(CH$_2$)$_n$—R9', wherein n=1–2 and the R9' is —X(CH$_2$)$_m$Y wherein X is —O—, —S—, —NH— or —N (alkyl)-substituent having 1–6 carbon atoms;

m=1–2;

Y is carboxyl, amido, sulpho, sulphamino, carboxyl, mercapto, carbylmercapto, amino, alkylamino, carbamino —PO(OH)$_2$, —PO(O—C$_1$-C$_6$-alkyl)$_2$, —PO(NH—C1-C6-alkyl)$_2$, PO(O—C,—C$_1$-C$_6$-alkyl)(NH—C1-6-alkyl), —PO(OH)(O—C$_1$-C$_6$-alkyl); —PO(OH)(NH—C$_1$-C$_6$-alkyl); wherein:

"halogen" is fluorine, bromine, chlorine, and iodine atoms;

"alkyl" is:
a) a branched or unbranched alkyl group having 1–6 carbon atoms,
b) a branched or unbranched alkenyl group having 2–6 carbon atoms, and
c) a branched or unbranched alkinyl group having 2–6 carbon atoms;

"substituted alkyl" is a branched or unbranched alkyl, alkenyl or alkinyl group having 1–6 carbon atoms and having substituted by one or more substituents selected from the group consisting of hydroxyl, mercapto, carbylmercapto, halogen, carbyloxy, amino, amido, carboxyl, cycloalkyl, sulpho or acyl;

"carbyloxy" is the group —OR$_a$, where R$_a$ is alkyl, substituted alkyl, aryl, substituted aryl, arylalkyl, substituted arylalkyl, cycloalkyl, substituted cycloalkyl, heterocycloalkyl or substituted heterocycloalkyl whereas these generic groups have meanings being identical with definitions of the corresponding groups as defined in this legend;

"carbylmercapto" is the group —SR$_b$ where R$_b$ is alkyl, substituted alkyl, aryl, substituted aryl, arylalkyl, substituted arylalkyl, cycloalkyl, substituted cycloalkyl, heterocycloalkyl or substituted heterocycloalkyl whereas these general groups have meanings being identical with definitions of the corresponding groups as defined in this legend;

"sulpho" is the group —SO$_3$R$_c$ where R$_c$ is:
a) hydrogen,
b) a branched or unbranched alkyl group having 1–6 carbon atoms,
c) a branched or unbranched alkenyl group having 2–6 carbon atoms,
d) a branched or unbranched alkinyl group having 2–6 carbon atoms, and
e) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl, whereas these generic groups have meanings being identical with the definitions of the corresponding groups as defined in this legend;

"sulphamino" is the group —NHSO$_3$R$_d$ wherein R$_d$ is:
a) hydrogen,
b) a branched or unbranched alkyl group having 1–6 carbon atoms,
c) a branched or unbranched alkenyl group having 2–6 carbon atoms,
d) a branched or unbranched alkinyl group having 2–6 carbon atoms, and
e) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl, whereas these generic substituents have meanings being identical with definitions of the corresponding groups as defined in this legend;

"acyl" is, the group —C(O)R$_e$ where R$_e$ is hydrogen, alkyl, substituted alkyl, aryl, substituted aryl, arylalkyl, substituted arylalkyl, cycloalkyl, substituted cycloalkyl whereas these generic groups have meanings being identical with definitions of the corresponding groups as defined in this legend;

"aryloxy" is the group —OAr, where Ar is an aryl, substituted aryl, heteroaryl or substituted heteroaryl whereas these generic groups have meanings being identical with definitions of the corresponding groups as defined in this legend;

"alkylamino" is the group —NR$_f$R$_g$ where R$_f$ and R$_g$, that are independent of one another, represent hydrogen, alkyl, substituted alkyl, provided that R$_f$ and R$_g$ are not both hydrogens;

"amido" is the group —C(O)NR$_h$R$_i$', where R$_h$ and R$_i$' may independently be hydrogen, alkyl, substituted alkyl, aryl, substituted aryl, heteroaryl, substituted heteroaryl whereas these generic groups have meanings being identical with definitions of the corresponding groups as defined in this legend;

"carboxyl" is the group —C(O)OR$_j$ where R$_j$ is hydrogen, alkyl, substituted alkyl, aryl, substituted aryl, heteroaryl or substituted heteroaryl;

"carbamino" is the group —NHCOR$_k$ where R$_k$ may be hydrogen, alkyl, substituted alkyl, heterocycle, aryl, substituted aryl, heteroaryl and substituted heteroaryl whereas these generic groups have meanings being identical with definitions of the corresponding groups as defined in this legend;

"aryl" is an aromatic carbocyclic group having from 6 to 18 carbon atoms and being composed of at least one aromatic or multiple condensed rings in which at least one of which being aromatic;

"substituted aryl" is an aromatic carbocyclic group having from 6 to 18 carbon atoms and being composed of at least one aromatic ring or of multiple condensed rings at least one of which being aromatic; The ring(s) are optionally substituted with one or more substituents selected from the group consisting of halogen, alkyl, hydroxyl, carbylmercapto, alkylamino, carbyloxy, amino, amido, carboxyl, nitro, mercapto or sulpho;

"heterocycle" is a heterocyclic group having from 4 to 9 carbon atoms and at least one heteroatom selected from the group consisting of N, O or S;

"heteroaryl" is a heterocyclic group having from 4 to 9 carbon atoms and at least one heteroatom selected from the group consisting of N, O or S with at least one ring of this group being aromatic;

"substituted heteroaryl" is a heterocyclic group having from 4 to 9 carbon atoms and at least one heteroatom selected from the group consisting of N, O or S with at least one ring of this group being aromatic and this group being substituted with one or more substituents selected from the group consisting of halogen, alkyl, carbyloxy, carbylmercapto, alkylamino, amido, carboxyl, hydroxyl, nitro, mercapto or sulpho;

"arylalkyl" is the group —R$_j$—Ar wherein R$_j$ is:
a) a branched or unbranched alkyl group having 1–6 carbon atoms,
b) a branched or unbranched alkenyl group having 2–6 carbon atoms,
c) a branched or unbranched alkinyl group having 2–6 carbon atoms;

"Ar" is an aromatic carbocyclic group having from 6–18 carbon atoms and being composed of at least one aromatic ring or of multiple condensed rings at least one of which being aromatic and the group being optionally substituted with one or more substituents selected from the group consisting of halogen, alkyl, hydroxyl, carbylmercapto, alkylamino, carbyloxy, amino, amido, carboxyl, nitro, mercapto or sulpho;

"heteroalkyl" is the group —R$_m$—L wherein R$_m$ is:
a) a branched or unbranched alkyl group having 1–6 carbon atoms,
b) a branched or unbranched alkenyl group having 2–6 carbon atoms,
c) a branched or unbranched alkinyl group having 2–6 carbon atoms,
d) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl; and L is a heterocyclic group having from 4 to 9 carbon atoms and at least one heteroatom selected from the group consisting of N, O or S and the group being unsubstituted or substituted with one or more substituents selected from the group consisting of halogen, alkyl, alkoxy, alkylmercapto, alkylamino, amido, carboxyl, hydroxy, nitro, mercapto or sulpho;

"heteroarylalkyl" is the group —R$_n$—G wherein R$_n$ is
a) a branched or unbranched alkyl group having 1–6 carbon atoms,
b) a branched or unbranched alkenyl group having 2–6 carbon atoms,
c) a branched or unbranched alkinyl group having 2–6 carbon atoms,
d) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl; and G is a heterocyclic group having from 4 to 9 carbon atoms and at least one heteroatom selected from the group consisting of N, O or S with at least one ring of which being aromatic and the group being optionally substituted with one or more substituents selected from the group consisting of halogen, alkyl, carbyloxy, carbylmercapto, alkylamino, amido, carboxyl, hydroxyl, nitro, mercapto or sulpho;

"cycloalkyl" is a monocyclic or polycyclic alkyl group containing 3 to 15 carbon atoms;

"substituted cycloalkyl" is a monocyclic or polycyclic alkyl group containing 3 to 15 carbon atoms and being substituted by one or more substituents selected from the group consisting of halogen, alkyl, substituted alkyl, carbyloxy, carbylmercapto, aryl, nitro, mercapto or sulpho;

"heterocycloalkyl" is a monocyclic or polycyclic alkyl group containing 3 to 15 carbon atoms which at least one ring carbon atom of its cyclic structure being replaced with a heteroatom selected from the group consisting of N, O, S or P;

"substituted heterocycloalkyl" is a monocyclic or polycyclic alkyl group containing 3 to 15 carbon atoms which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulpho;

"cycloalkyl alkyl" is the group —$R_o$—J where $R_o$ is:
a) a branched or unbranched alkyl group having 1–6 carbon atoms,
b) a branched or unbranched alkenyl group having 2–6 carbon atoms,
c) a branched or unbranched alkinyl group having 2–6 carbon atoms,
d) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl, whereas these generic substituent group have meanings being identical with definitions of the corresponding groups as defined in this legend; and J is:
a) a monocyclic or polycyclic alkyl group containing 3 to 15 carbon atoms; and
b) a monocyclic or polycyclic alkyl group containing 3 to 15 carbon atoms which contains one or more substituents selected from the group consisting of halogen, alkyl, substituted alkyl, carbyloxy, carbylmercapto, aryl, nitro, mercapto or sulpho;

"heterocycloalkylalkyl" is the group —$R_p$V where $R_p$ is:
a) a branched or unbranched alkyl group having 1–6 carbon atoms,
b) a branched or unbranched alkenyl group having 2–6 carbon atoms,
c) a branched or unbranched alkinyl group having 2–6 carbon atoms, and
d) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl; and V is:
a) a monocyclic or polycyclic alkyl group containing 3 to 15 carbon atoms with at least one being replaced with a heteroatom selected from the group consisting of N, O, S or P; and
b) a monocyclic or polycyclic alkyl group containing 3 to 15 carbon atoms with at least one being replaced with a heteroatom selected from the group consisting of N, O, S or P and the group contains one or more substituents selected from the group consisting of halogen, alkyl, substituted alkyl, carbyloxy, carbylmercapto, aryl, nitro, mercapto or sulpho.

2. Substituted nitrogen heterocyclic derivatives of the formula I according to claim 1, wherein R6=H.

3. Substituted nitrogen heterocyclic derivatives of the formula I according to claim 1, wherein R2=H and R6, R8 and R9 are as defined in claim 1.

4. Substituted nitrogen heterocyclic derivatives according to claim 1 of the formula Ia,

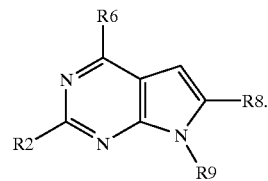

(Ia)

5. Substituted nitrogen heterocylic derivatives of the formula Ia according to claim 4, wherein R6=H.

6. Substituted nitrogen heterocylic derivatives of the formula Ia according to claim 4, wherein R2=H.

7. Substituted nitrogen heterocyclic derivatives according to claim 1 of the formula Ic,

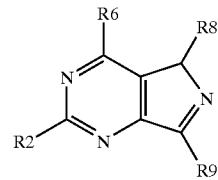

(Ic)

wherein R2, R6, R8 and R9 are as defined above in claim 1.

8. Substituted nitrogen heterocyclic derivatives of the formula Ic according to claim 7, wherein R6=H.

9. Substituted nitrogen heterocyclic derivatives of the formula Ic according to claim 7, wherein R2=H.

10. Substituted nitrogen heterocyclic derivatives according to claim 1 of the formula Id,

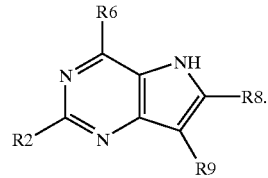

(Id)

11. Substituted nitrogen heterocyclic derivatives of the formula Id according to claim 10, wherein R6=H.

12. Substituted nitrogen heterocyclic derivatives of the formula Id according to claim 10, wherein R2=H.

13. Substituted nitrogen heterocyclic derivatives according to claim 1 of the formula If,

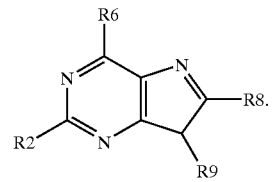

(If)

14. Substituted nitrogen heterocyclic derivatives of the formula If according to claim 13, wherein R6=H.

15. Substituted nitrogen heterocyclic derivatives of the formula If according to claim 13, wherein R2=H.

16. Substituted nitrogen heterocyclic derivatives of the formula I

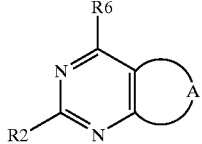
(I)

wherein

A is a divalent group selected from the ensemble consisting of

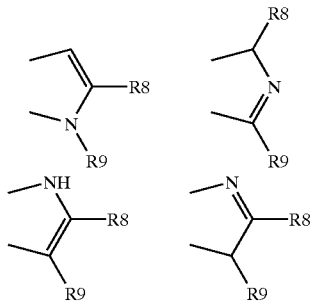

Z is N;

R2 and R6 are independent of one another, and represent H, halogen, alkyl, substituted alkyl, cycloalkyl, substituted cycloalkyl, cycloalkyl alkyl, arylalkyl, heteroalkyl, heteroarylalkyl, heterocycloalkyl alkyl or R6'—X, wherein X is an —NH—, —N(C,-C$_6$-alkyl)—, —O— or —S— moiety;

R6' is H, alkyl, substituted alkyl, acyl, amido, sulpho, cycloalkyl, substituted cycloalkyl, aryl, substituted aryl, heterocycle, heteroaryl, substituted heteroaryl, arylalkyl, heterocycloalkyl, substituted heterocycloalkyl, heteroarylalkyl, heteroalkyl, cycloalkyl alkyl and heterocycloalkyl alkyl; and R8 is halogen, hydroxyl, amino, carboxyl, cyano, nitro, amido, sulpho, sulphamino, carbamino, substituted alkyl, cycloalkyl, substituted cycloalkyl, arylalkyl, heteroalkyl, heteroarylalkyl, cycloalkyl alkyl, heterocycloalkyl alkyl or R8'—X, wherein X is —NH—, —N(alkyl)-, —O— or —S— moiety and R8' is according to any one of the substituents defined above for R2 or R6'; and R9 is alkyl, acyl, carboxyl, amido, sulphamino, cycloalkyl, substituted cycloalkyl, cycloalkyl alkyl, heteroalkylcycloalkyl alkyl, heterocycloalkyl, substituted heterocycloalkyl, aryl, substituted aryl, heterocycle, heteroaryl, substituted heteroaryl, or —B—R9' wherein B is —CH$_2$—, —(CH$_2$)$_2$—, —CH(CH$_3$)CH$_2$—, —CH(CH$_2$F)CH$_2$—, —CH(CH$_2$OH) CH$_2$—, or the groups of the following structure

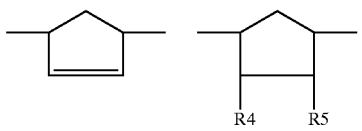

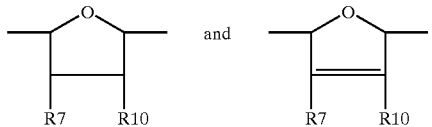

wherein the left hand bond is linked to nitrogen of 5-membered ring of compounds of the formula I; and wherein R4 and R5, that are independent of one another, represent hydrogen, hydroxyl, halogen, amino, acyloxy substituents having 1–5 carbon atoms, alkoxy substituents having 1–5 carbon atoms, alkylmercapto substituents having 1–5 carbon atoms, alkylamino substituents having 1–5 carbon atoms and dialkylamino in which each alkyl substituent has 1–5 carbon atoms;

R7 and R10, that are independent of one another, represent H or alkyl substituent having 1–10 carbon atoms;

or R9 is —(CH$_2$)$_n$—R9', wherein n=1–2 and the R9' is —X(CH$_2$)$_m$Y wherein X is —O—, —S—, —NH— or —N(alkyl)- substituent having 1–6 carbon atoms;

m=1–2;

Y is carboxyl, amido, sulpho, sulphamino, carboxyl, mercapto, carbylmercapto, amino, alkylamino, carbamino —PO(OH)$_2$, —PO(O—C$_1$-C$_6$-alkyl)$_2$, —PO(NH—C1–C6-alkyl)$_2$, PO(O—C,—C$_1$-C$_6$-alkyl)(NH—C1-6-alkyl), —PO(OH)(O—C$_1$-C$_6$-alkyl); —PO(OH)(NH—C$_1$-C$_6$-alkyl); wherein:

"halogen" is fluorine, bromine, chlorine, and iodine atoms;

"alkyl" is:
  a) a branched or unbranched alkyl group having 1–6 carbon atoms,
  b) a branched or unbranched alkenyl group having 2–6 carbon atoms, and
  c) a branched or unbranched alkinyl group having 2–6 carbon atoms;

"substituted alkyl" is a branched or unbranched alkyl, alkenyl or alkinyl group having 1–6 carbon atoms and having substituted by one or more substituents selected from the group consisting of hydroxyl, mercapto, carbylmercapto, halogen, carbyloxy, amino, amido, carboxyl, cycloalkyl, sulpho or acyl;

"carbyloxy" is the group —OR$_a$, where R$_a$ is alkyl, substituted alkyl, aryl, substituted aryl, arylalkyl, substituted arylalkyl, cycloalkyl, substituted cycloalkyl, heterocycloalkyl or substituted heterocycloalkyl whereas these generic groups have meanings being identical with definitions of the corresponding groups as defined in this legend;

"carbylmercapto" is the group —SR$_b$ where R$_b$ is alkyl, substituted alkyl, aryl, substituted aryl, arylalkyl, substituted arylalkyl, cycloalkyl, substituted cycloalkyl, heterocycloalkyl or substituted heterocycloalkyl whereas these general groups have meanings being identical with definitions of the corresponding groups as defined in this legend;

"sulpho" is the group —SO$_3$R$_c$ where R$_c$ is:
  a) hydrogen,
  b) a branched or unbranched alkyl group having 1–6 carbon atoms,
  c) a branched or unbranched alkenyl group having 2–6 carbon atoms, d) a branched or unbranched alkinyl group having 2–6 carbon atoms, and e) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl, whereas these generic groups have meanings being identical with the definitions of the corresponding groups as defined in this legend;

"sulphamino" is the group —NHSO$_3$R$_d$ wherein R$_d$ is:
a) hydrogen,
b) a branched or unbranched alkyl group having 1–6 carbon atoms,
c) a branched or unbranched alkenyl group having 2–6 carbon atoms,
d) a branched or unbranched alkinyl group having 2–6 carbon atoms, and
e) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl, whereas these generic substituents have meanings being identical with definitions of the corresponding groups as defined in this legend;

"acyl" is the group —C(O)R$_e$ where R$_e$ is hydrogen, alkyl, substituted alkyl, aryl, substituted aryl, arylalkyl, substituted arylalkyl, cycloalkyl, substituted cycloalkyl whereas these generic groups have meanings being identical with definitions of the corresponding groups as defined in this legend;

"aryloxy" is the group —OAr, where Ar is an aryl, substituted aryl, heteroaryl or substituted heteroaryl whereas these generic groups have meanings being identical with definitions of the corresponding groups as defined in this legend;

"alkylamino" is the group —NR$_f$R$_g$ where R$_f$ and R$_g$, that are independent of one another, represent hydrogen, alkyl, substituted alkyl, provided that R$_f$ and R$_g$ are not both hydrogens;

"amido" is the group —C(O)NR$_h$R$_i$', where R$_h$ and R$_i$' may independently be hydrogen, alkyl, substituted alkyl, aryl, substituted aryl, heteroaryl, substituted heteroaryl whereas these generic groups have meanings being identical with definitions of the corresponding groups as defined in this legend;

"carboxyl" is the group —C(O)OR$_j$ where R$_j$ is hydrogen, alkyl, substituted alkyl, aryl, substituted aryl, heteroaryl or substituted heteroaryl;

"carbamino" is the group —NHCOR$_k$ where R$_k$ may be hydrogen, alkyl, substituted alkyl, heterocycle, aryl, substituted aryl, heteroaryl and substituted heteroaryl whereas these generic groups have meanings being identical with definitions of the corresponding groups as defined in this legend;

"aryl" is an aromatic carbocyclic group having from 6 to 18 carbon atoms and being composed of at least one aromatic or multiple condensed rings in which at least one of which being aromatic;

"substituted aryl" is an aromatic carbocyclic group having from 6 to 18 carbon atoms and being composed of at least one aromatic ring or of multiple condensed rings at least one of which being aromatic; The ring(s) are optionally substituted with one or more substituents selected from the group consisting of halogen, alkyl, hydroxyl, carbylmercapto, alkylamino, carbyloxy, amino, amido, carboxyl, nitro, mercapto or sulpho;

"heterocycle" is a heterocyclic group having from 4 to 9 carbon atoms and at least one heteroatom selected from the group consisting of N, O or S;

"heteroaryl" is a heterocyclic group having from 4 to 9 carbon atoms and at least one heteroatom selected from the group consisting of N, O or S with at least one ring of this group being aromatic;

"substituted heteroaryl" is a heterocyclic group having from 4 to 9 carbon atoms and at least one heteroatom selected from the group consisting of N, O or S with at least one ring of this group being aromatic and this group being substituted with one or more substituents selected from the group consisting of halogen, alkyl, carbyloxy, carbylmercapto, alkylamino, amido, carboxyl, hydroxyl, nitro, mercapto or sulpho;

"arylalkyl" is the group —R$_j$—Ar wherein R$_j$ is:
a) a branched or unbranched alkyl group having 1–6 carbon atoms,
b) a branched or unbranched alkenyl group having 2–6 carbon atoms,
c) a branched or unbranched alkinyl group having 2–6 carbon atoms;

"Ar" is an aromatic carbocyclic group having from 6–18 carbon atoms and being composed of at least one aromatic ring or of multiple condensed rings at least one of which being aromatic and the group being optionally substituted with one or more substituents selected from the group consisting of halogen, alkyl, hydroxyl, carbylmercapto, alkylamino, carbyloxy, amino, amido, carboxyl, nitro, mercapto or sulpho;

"heteroalkyl" is the group —R$_m$—L wherein R$_m$ is:
a) a branched or unbranched alkyl group having 1–6 carbon atoms,
b) a branched or unbranched alkenyl group having 2–6 carbon atoms,
c) a branched or unbranched alkinyl group having 2–6 carbon atoms,
d) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl; and L is a heterocyclic group having from 4 to 9 carbon atoms and at least one heteroatom selected from the group consisting of N, O or S and the group being unsubstituted or substituted with one or more substituents selected from the group consisting of halogen, alkyl, alkoxy, alkylmercapto, alkylamino, amido, carboxyl, hydroxy, nitro, mercapto or sulpho;

"heteroarylalkyl" is the group —R$_n$—G wherein R$_n$ is
a) a branched or unbranched alkyl group having 1–6 carbon atoms,
b) a branched or unbranched alkenyl group having 2–6 carbon atoms, c) a branched or unbranched alkinyl group having 2–6 carbon atoms,
d) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl; and G is a heterocyclic group having from 4 to 9 carbon atoms and at least one heteroatom selected from the group consisting of N, O or S with at least one ring of which being aromatic and the group being optionally substituted with one or more substituents selected from the group consisting of halogen, alkyl, carbyloxy, carbylmercapto, alkylamino, amido, carboxyl, hydroxyl, nitro, mercapto or sulpho;

"cycloalkyl" is a monocyclic or polycyclic alkyl group containing 3 to 15 carbon atoms;

"substituted cycloalkyl" is a monocyclic or polycyclic alkyl group containing 3 to 15 carbon atoms and being substituted by one or more substituents selected from the group consisting of halogen, alkyl, substituted alkyl, carbyloxy, carbylmercapto, aryl, nitro, mercapto or sulpho;

"heterocycloalkyl" is a monocyclic or polycyclic alkyl group containing 3 to 15 carbon atoms which at least one ring carbon atom of its cyclic structure being replaced with a heteroatom selected from the group consisting of N, O, S or P;

"substituted heterocycloalkyl" is a monocyclic or polycyclic alkyl group containing 3 to 15 carbon atoms which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulpho;

"cycloalkyl alkyl" is the group —$R_o$—J where $R_o$ is:
a) a branched or unbranched alkyl group having 1–6 carbon atoms,
b) a branched or unbranched alkenyl group having 2–6 carbon atoms,
c) a branched or unbranched alkinyl group having 2–6 carbon atoms,
d) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl, whereas these generic substituent group have meanings being identical with definitions of the corresponding groups as defined in this legend; and J is:
a) a monocyclic or polycyclic alkyl group containing 3 to 15 carbon atoms; and
b) a monocyclic or polycyclic alkyl group containing 3 to 15 carbon atoms which contains one or more substituents selected from the group consisting of halogen, alkyl, substituted alkyl, carbyloxy, carbylmercapto, aryl, nitro, mercapto or sulpho;

"heterocycloalkylalkyl" is the group —$R_p$V where $R_p$ is:

a) a branched or unbranched alkyl group having 1–6 carbon atoms,
b) a branched or unbranched alkenyl group having 2–6 carbon atoms,
c) a branched or unbranched alkinyl group having 2–6 carbon atoms, and
d) a branched or unbranched alkyl, alkenyl or alkinyl group having 1–6 carbon atoms and being substituted by one or more substituents selected from the group consisting of hydroxyl, mercapto, carbylmercapto, halogen, carbyloxy, amino, amido, carboxyl, cycloalkyl, sulpho or acyl; and V is:
a) a monocyclic or polycyclic alkyl group containing 3 to 15 carbon atoms with at least one being replaced with a heteroatom selected from the group consisting of N, O, S or P; and
b) a monocyclic or polycyclic alkyl group containing 3 to 15 carbon atoms with at least one being replaced with a heteroatom selected from the group consisting of N, O, S or P and the group contains one or more substituents selected from the group consisting of halogen, alkyl, substituted alkyl, carbyloxy, carbylmercapto, aryl, nitro, mercapto or sulpho.

17. Substituted nitrogen heterocyclic derivatives of the formula I according to claim 16, wherein R6=H.

18. Substituted nitrogen heterocyclic derivatives of the formula I according to claim 16, wherein R2=H and R6, R8 and R9 are as defined in claim 16.

19. Substituted nitrogen heterocyclic derivatives according to claim 16 of the formula Ia,

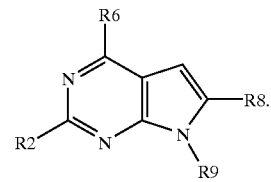

(Ia)

20. Substituted nitrogen heterocylic derivatives of the formula Ia according to claim 19, wherein R6=H.

21. Substituted nitrogen heterocylic derivatives of the formula Ia according to claim 19, wherein R2=H.

22. Substituted nitrogen heterocyclic derivatives according to claim 16 of the formula Ic,

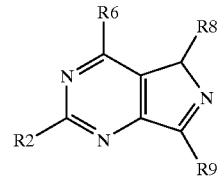

(Ic)

wherein R2, R6, R8 and R9 are as defined above in claim 16.

23. Substituted nitrogen heterocyclic derivatives of the formula Ic according to claim 22, wherein R6=H.

24. Substituted nitrogen heterocyclic derivatives of the formula Ic according to claim 22, wherein R2=H.

25. Substituted nitrogen heterocyclic derivatives according to claim 16 of the formula Id,

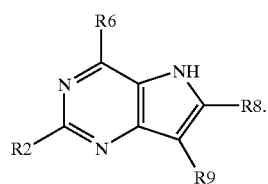 (Id)

26. Substituted nitrogen heterocyclic derivatives of the formula Id according to claim 25, wherein R6=H.

27. Substituted nitrogen heterocyclic derivatives of the formula Id according to claim 25, wherein R2=H.

28. Substituted nitrogen heterocyclic derivatives according to claim 16 of the formula If,

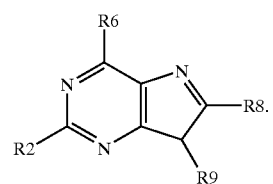 (If)

29. Substituted nitrogen heterocyclic derivatives of the formula If according to claim 28, wherein R6=H.

30. Substituted nitrogen heterocyclic derivatives of the formula If according to claim 28, wherein R2=H.

* * * * *